US008147805B2

(12) United States Patent
Yang et al.

(10) Patent No.: US 8,147,805 B2
(45) Date of Patent: Apr. 3, 2012

(54) CONJUGATES FOR DUAL IMAGING AND RADIOCHEMOTHERAPY: COMPOSITION, MANUFACTURING, AND APPLICATIONS

(75) Inventors: David Yang, Sugar Land, TX (US); Dongfang Yu, Houston, TX (US); Mithu Chanda, Houston, TX (US); Ali Azhdarinia, Houston, TX (US); Changsok Oh, Houson, TX (US); E. Edmund Kim, Houson, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1314 days.

(21) Appl. No.: 11/326,117

(22) Filed: Jan. 5, 2006

(65) Prior Publication Data

US 2006/0182687 A1 Aug. 17, 2006

Related U.S. Application Data

(60) Provisional application No. 60/641,559, filed on Jan. 5, 2005.

(51) Int. Cl.
*A61K 49/04* (2006.01)
*A61K 51/00* (2006.01)
*A61M 36/14* (2006.01)

(52) U.S. Cl. ............ 424/9.45; 424/1.11; 424/1.29; 424/1.37; 424/1.61; 424/1.65; 424/1.73; 424/9.4; 424/9.451; 424/9.452; 424/9.453; 424/9.454; 424/9.455

(58) Field of Classification Search ............ 424/1.11, 424/1.73, 9.3, 9.322, 9.323, 9.364, 9.4, 9.43, 424/9.45, 1.29, 1.37, 1.61, 1.65, 9.451, 9.452, 424/9.453, 9.454, 9.455
See application file for complete search history.

(56) References Cited

U.S. PATENT DOCUMENTS

| | | | |
|---|---|---|---|
| 4,861,869 A | 8/1989 | Nicolotti et al. | 424/1.53 |
| 4,965,392 A | 10/1990 | Fritzberg et al. | 558/254 |
| 4,986,980 A * | 1/1991 | Jacobsen | 424/9.35 |
| 5,032,678 A | 7/1991 | Washino et al. | 534/14 |
| 5,089,604 A | 2/1992 | Washino et al. | 530/395 |
| 5,118,798 A | 6/1992 | Washino et al. | 530/363 |
| 5,268,163 A | 12/1993 | Verbruggen | 534/14 |
| 5,271,924 A * | 12/1993 | Hashiguchi et al. | 424/9.35 |
| 5,364,613 A * | 11/1994 | Sieving et al. | 424/9.3 |
| 5,397,563 A | 3/1995 | Rogers, Jr. et al. | 424/9.37 |
| 5,538,712 A | 7/1996 | Wenzel et al. | 424/1.45 |
| 5,605,672 A | 2/1997 | Bogdanov et al. | 424/1.65 |
| 5,900,228 A | 5/1999 | Meade et al. | 424/9.363 |
| 5,955,053 A | 9/1999 | Marzilli et al. | 424/1.11 |
| 5,986,074 A | 11/1999 | Marzilli et al. | 534/14 |
| 6,123,921 A | 9/2000 | Meade et al. | 424/9.363 |
| 6,399,951 B1 | 6/2002 | Paulus et al. | 250/370.13 |
| 6,521,209 B1 | 2/2003 | Meade et al. | 424/9.3 |
| 6,613,304 B2 | 9/2003 | Dolphin et al. | 424/1.65 |
| 6,623,721 B2 | 9/2003 | Flanagan et al. | 424/1.65 |
| 6,692,724 B1 | 2/2004 | Yang et al. | 424/1.49 |
| 6,770,259 B2 | 8/2004 | Carpenter, Jr. | 424/9.1 |
| 7,067,111 B1 | 6/2006 | Yang et al. | 424/9.1 |
| 7,303,741 B2 * | 12/2007 | Hancu et al. | 424/9.3 |
| 2003/0003048 A1 | 1/2003 | Li et al. | 424/1.49 |
| 2003/0198599 A1 | 10/2003 | Yalpani | 424/9.35 |
| 2003/0224974 A1 | 12/2003 | Bolotin | 514/6 |
| 2004/0022729 A1 * | 2/2004 | Uzgiris | 424/9.4 |
| 2004/0042959 A1 | 3/2004 | Montalto et al. | 424/1.11 |
| 2004/0166058 A1 | 8/2004 | Yang et al. | 424/1.49 |
| 2005/0024380 A1 | 2/2005 | Lin et al. | 345/600 |
| 2005/0036946 A1 * | 2/2005 | Pathak et al. | 424/9.4 |
| 2005/0079133 A1 | 4/2005 | Yang et al. | 424/1.49 |
| 2005/0129619 A1 | 6/2005 | Yang et al. | 424/9.34 |
| 2005/0265922 A1 * | 12/2005 | Nie et al. | 424/1.11 |

FOREIGN PATENT DOCUMENTS

| | | |
|---|---|---|
| WO | WO 94/28940 | 12/1994 |
| WO | WO 02/087498 | 11/2002 |
| WO | WO 02/091807 | 11/2002 |
| WO | WO 03/082301 | 10/2003 |
| WO | WO 2004/026344 | 4/2004 |
| WO | WO 2004/044227 | 5/2004 |

OTHER PUBLICATIONS de Crespigny et al., Magnetic Resonance Imaging, (1999), 17, p. 1297-1305.*
Woldhuis et al., Pflugers Arch., 1993, 425(3-4), p. 191-8 (abstract).*
Huber, M. et al., Bioconjugate Chem., 1998, 9, p. 242-249.*
Bayly et al., "Carbohydrate Conjugates for Molecular Imaging and Radiotherapy: 99mTc(I) and 186Re(I) Tricarbonyl Complexes of N-(2'-Hydroxybenzyl-2-amino-2-deoxy-D-glucose," *Bioconjugate Chem.*, 15:923-926, 2004.
Gardiner, "The therapeutic potential of synthetic multivalent carbohydrates," *Exp. Opin. Invest. Drugs*, 7:405-411, 1998.
Perin et al., "Influence of Technetium-99m-Labeling Conditions on Physico-Chemical and Related Biological Properties of an Acylated Poly-Galactosidic Macrophage Targeting Agent for Inflammation Imaging," *Nuclear Med. Biol.*, 23:947-955, 1996.
Alberico et al. "Imaging in head and neck oncology," *Surg. Oncol. Clin. N. Am.*, 13(1):13-35, 2004.
Benard et al., "Imaging gliomas with positron emission tomography and single-photon emission computed tomography," *Semin. Nucl. Med.*, 33(2):148-162, 2003.

(Continued)

*Primary Examiner* — Michael G Hartley
*Assistant Examiner* — Leah Schlientz
(74) *Attorney, Agent, or Firm* — Fulbright & Jaworski LLP

(57) ABSTRACT

Compositions and methods for dual imaging and for dual chemotherapy and radiotherapy are disclosed. More particularly, the invention concerns compounds comprising the structure $X_1—Y—X_2$, wherein Y comprises two or more carbohydrate residues covalently attached to one another, $X_1$ and $X_2$ are diagnostic or therapeutic moieties covalently attached to Y, provided that when Y does not comprise a glucosamine residue, $X_1$ and $X_2$ are diagnostic moieties. The present invention also concerns methods of synthesis of these compounds, application of such compounds for dual imaging and treatment of hyperproliferative disease, and kits for preparing a radiolabeled therapeutic or diagnostic compound.

10 Claims, 9 Drawing Sheets

OTHER PUBLICATIONS

Bolhuis et al., "Adoptive immunotherapy of ovarian carcinoma with bs-MAb-targeted lymphocytes: a multicenter study," *Int. J. Cancer Suppl.*, 7:78-81, 1992.

Bush et al., "Definitive evidence for hypoxic cells influencing cure in cancer therapy," *Br. J. Cancer Suppl.*, 37(3):302-306, 1978.

Campbell et al., "Folate-binding protein is a marker for ovarian cancer," *Cancer Res.*, 51(19):5329-5338 1991.

Canevari et al., "Ovarian carcinoma therapy with monoclonal antibodies," *Hybridoma.*, 12(5):501-507, 1993.

Coney et al., "Chimerica murine-human antibodies directed against folate binding receptor are efficient mediators of ovarian carcinoma cell killing," *Cancer Res.*, 54(9):2448-2455, 1994.

Conti, "Introduction to imaging brain tumor metabolism with positron emission tomography (PET)," *Cancer Invest.*, 13(2):244-259, 1995.

Deng and Lizzi, "A review of physical phenomena associated with ultrasonic contrast agents and illustrative clinical applications," *Ultrasound Med. Biol.*, 28(3):277-286, 2002.

Dische, "A review of hypoxic cell radiosensitization," *Int. J. Radiat. Oncol. Biol. Phys.*, 20(1):147-152, 1991.

Forsberg et al., "Quantitative acoustic characterization of a new surfactant-based ultrasound contrast agent," *Ultrasound Med. Biol.*, 23(8):1201-1208, 1997.

Franklin et al., "New anti-lung-cancer antibody cluster 12 reacts with human folate receptors present on adenocarcinoma," *Int. J. Cancer Suppl.*, 8:89-95, 1994.

Gatenby et al., "Oxygen distribution in squamous cell carcinoma metastases and its relationship to outcome of radiation therapy," *Int. J. Radiat. Oncol. Biol. Phys.*, 14(5):831-838, 1988.

Ginobbi et al., "Folic acid-polylysine carrier improves efficacy of c-myc antisense oligodeoxynucleotides on human melanoma (M14) cells," *Anticancer Res.*, 17(1A):29-35, 1997.

Goldberg et al., "Ultrasound contrast agents: a review," *Ultrasound Med. Biol.*, 20(4):319-333, 1994.

Goldberg., "Should clinical cardiologists incorporate the proximal isovelocity surface area (PISA) method into their ever enlarging armamentarium?" *Heart*, 78(3):209-210, 1997.

Gray et al., "Effect of nitric oxide on the radiosensitivity of tumour cells," *Nature*, 182(4640):952-953, 1958.

Hall et al., "Radiation response characteristics of human cells in vitro," *Radiat. Res.*, 114(3):415-424 1988.

Henson et al., "Gadolinium-enhanced CT angiography of the circle of Willis and Neck," *AJNR Am J. Neuroradiol.*, 25(6):969-972, 2004.

Holm et al., "Folate receptor of human mannary adenocarcinoma," *APMIS*, 102(6):413-419, 1994.

Hsueh and Dolnick, "Altered folate-binding protein mRNA stability in KB cells grown in folate-deficient medium," *Biochem. Pharmacol.*, 45(12):2537-2545, 1993.

Koh et al., "Imaging of hypoxia in human tumors with [F-18] fluoromisonidazole," *Int. J. Radiat. Oncol. Biol. Phys.*, 22:199-212, 1992.

Kranz et al., "Conjugates of folate and anti-T-cell-receptor antibodies specifically target folate-receptor-positive tumor cells for lysis," *Proc. Natl. Acad. Sci USA*, 92(20):9057-9061, 1995.

Labbe, "SPECT/CT emerges from the shadow of PET/CT," *Biophotonics International*, Jun. 2003.

Leamon and Low, "Cytotoxicity of Momordin-Folate conjugates in cultured human cells," *J. Biol. Chem.*, 267(35):24966-24971, 1992.

Leamon and Low, "Delivery of macromolecules into living cells: A method that exploits folate receptor endocytosis," *Proc. Natl. Acad. Sci. USA*, 88(13):5572-5576, 1991.

Leamon and Low, "Membrane folate-binding proteins are responsible for folate-protein conjugate endocytosis into cultured cells," *Biochem. J.*, 291 ( Pt 3):855-860, 1993.

Leamon and Low, "Selective targeting of malignant cells with cytotoxin-folate conjugates," *J. Drug Target.*, 2(2):101-112, 1994.

Martin et al., "Enhanced binding of the hypoxic cell marker [3H] fluoromisonidazole in ischemic myocardium," *J. Nucl. Med.*, 30:194-201, 1989.

Nordsmark et al., "Pretreatment oxygenation predicts radiation response in advanced squamous cell carcinoma of the head and neck," *Radiother. Oncol.*, 41(1):31-39, 1996.

Ophir and Parker, "Contrast agents in diagnostic ultrasound," *Ultrasound Med. Biol.*, 15(4):319-333, 1989.

Orr et al., "Similarity of folate receptor expression in UMSCC 38 cells to squamous cell carcinoma differentiation markers," *J. Natl. Cancer Inst.*, 87(4):299-303, 1995.

Patrick et al., "Folate receptors as potential therapeutic targets in choroid plexus tumors of SV40 transgenic mice," *J. Neurooncol.*, 32(2):111-123, 1997.

Rasey et al., "Radiolabelled fluoromisonidazole as an imaging agent for tumor hypoxia," *Int. J. Radiat. Oncol. Biol. Phys.*, 17(5):985-991, 1989.

Rasey et al., "Response of mouse tissues to neutron and gamma radiation: protection by WR-3689 and WR-77913," *Radiother. Oncol.*, 17(2):167-173, 1990.

Ross et al., "Differential regulation of folate receptor isoforms in normal and malignant tissues in vivo and in established cell lines. Physiologic and clinical implications," *Cancer*, 73(9):2432-2443, 1994.

Saha et al., Radiopharmaceuticals for brain imaging, *Semin. Nucl. Med.*, 24(4):324-349 ,1994.

Song et al., "Prognostication of recovery in patients with acute ischemic stroke through the use of brain SPECT with technetium-99m—labeled metronidazole," *Stroke*, 34:982-986, 2003.

Strunk and Schild, "Actual clinical use of gadolinium-chelates for non-MRI applications," *Eur. Radiol.*, 14(6):1055-1062, 2004.

Taylor et al., "$^{99m}$Tc-MAEC complexes: new renal radiopharmaceuticals combining characteristics of $^{99m}$Tc-MAG3 and $^{99m}$Tc-EC," *J. Nucl. Med.*, 45:885-891, 2004.

Valk et al., "Hypoxia in human gliomas: demonstration by PET with fluorine-18-fluoromisonidazole," *J. Nucl. Med.*, 33(12):2133-2137, 1992.

Weitman et al., "Cellular localization of the folate receptor: potential role in drug toxicity and folate homeostasis," *Cancer Res.*, 52(23):6708-6711, 1992.

Weitman et al., "Distribution of the folate receptor GP38 in normal and malignant cell lines and tissues," *Cancer Res.*, 52(12):3396-3401 1992.

Weitman et al., "The folate receptor in central nervous system malignancies of childhood," *J Neurooncol.*, 21(2):107-112, 1994.

Westerhof et al., "Membrane transport of natural folates and antifolate compounds in murine L1210 leukemia cells: role of carrier- and receptor-mediated transport systems," *Cancer Res.*, 51(20):5507-5513, 1991.

Yang et al., "Associated alterations of striatal dopamine $D_2/D_3$ receptor and transporter binding in drug-naïve patients with schizophrenia: a dual-isotope SPECT study," *Am. J. Psychiatry*, 161:1496-1498, 2004.

Yang et al., "Imaging with 99mTc ECDG targeted at the multifunctional glucose transport system: feasibility study with rodents," *Radiology*, 226(2):465-473, 2003.

Yang et al., "IP6-induced growth inhibition and differentiation of HT-29 human colon cancer cells: involvement of intracellular inositol phosphates," *Anticancer Res.*, 15:2479-2488, 1995.

\* cited by examiner

Fig 1. Chemical Synthesis of EC-OS-DZ

Fig 2. Chemical Synthesis of EC-OS-Methotrexate

Fig 5. HPLC chromatogram of MTX
- Mobile phase- water(60%), acetonitrile(40%)
- Flow rate: 1ml/min
- Column C18, 4.6x250mm Fig 6. HPLC chromatogram of EC-OS-MTX (28% w/w MTX eq)

- Mobile phase- water(60%), acetonitrile(40%)
- Flow rate: 1ml/min
- Column C18, 4.6x250mm

CONJUGATES FOR DUAL IMAGING AND RADIOCHEMOTHERAPY: COMPOSITION, MANUFACTURING, AND APPLICATIONS

This patent application is related to U.S. Provisional Patent 60/641,559, filed on Jan. 5, 2005, which is herein incorporated by reference in its entirety.

BACKGROUND OF THE INVENTION

1. Field of the Invention

The present invention relates generally to the fields of radioimaging, radiotherapy, labeling, chemotherapy, and chemical synthesis. More particularly, the invention concerns certain novel compounds suitable for single or multimodality imaging, radiochemotherapy, and therapy of hyperproliferative disorders. The compounds are of the general structure $X_1$—Y—$X_2$, wherein Y comprises two or more carbohydrate residues covalently attached to one another to form a carbohydrate backbone, and $X_1$ and $X_2$ are diagnostic or therapeutic moieties covalently attached to Y, provided that when Y does not comprise a glucosamine residue, $X_1$ and $X_2$ are diagnostic moieties. The present invention also concerns methods of synthesis of these compounds and kits for preparing these compounds.

2. Description of Related Art

Biomedical imaging includes various modalities that are widely used by physicians and researchers to assist with not only the diagnosis of disease in a subject, but also to gain a greater understanding of normal structure and function of the body.

One such imaging modality that has been widely used is computerized tomography (CT). CT, developed in the 1970's, was the first imaging modality which marked a substantial improvement in medical imaging technology. By taking a series of X-rays, sometimes more than a thousand, from various angles and then combining them with a computer, CT made it possible to build up a three-dimensional image of any part of the body. Physicians could then instruct the computer to display two-dimensional slices from any angle and at any depth.

In CT, intravenous injection of a radiopaque contrast agent can assist in identifying a suspected soft tissue mass when initial CT scans are not diagnostic. Similarly, contrast agents aid in assessing the vascularity of a soft tissue or bone lesion. For example, the use of contrast agents may allow delineation of the relationship of a tumor and adjacent vascular structures.

In the early 1980s, CT was joined by magnetic resonance imaging (MRI), a clinical diagnostic and research procedure that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images. Examples of MRI contrast agents include gadolinium chelates, manganese chelates, chromium chelates, and iron particles. Although CT and MRI are useful in providing anatomical localization of lesions, the contrast media for these imaging modalities does not provide cellular target information.

Imaging modalities that provide information pertaining to information at the cellular level, such as cellular viability, include positron emission tomography (PET) and single-photon emission computed tomography (SPECT). In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high. Closely related to PET is single-photon emission computed tomography, or SPECT. The major difference between the two is that instead of a positron-emitting substance, SPECT uses a radioactive tracer that emits high-energy photons. SPECT is valuable for diagnosing coronary artery disease, and already some 2.5 million SPECT heart studies are done in the United States each year.

Optical imaging is another imaging modality that has gained widespread acceptance in particular areas of medicine. Examples include fluorescein angiography and indocyanine green angiography.

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues, and organs.

Ultrasound imaging of blood flow can be limited by a number of factors such as size and depth of the blood vessel. Ultrasonic contrast agents, a relatively recent development, include perfluorinated contrast agents, which are designed to overcome these limitations by helping to enhance grey-scale images and Doppler signals (Deng and Lizzi, 2002; Ophir and Parker, 1989; Goldberg et al., 1994; Goldberg, 1997; Forsberg, 1997).

The combination of more than one imaging modality can allow for the simultaneous acquisition of anatomical information and cellular information, thus allowing for improved resolution of a lesion of interest. Therefore, dual agents can be of particular value in the imaging of tumors. Furthermore, these agents also have the potential to reduce cost and lessen patient inconvenience. The patient would avoid the need to be injected twice. There may be cost savings to the patient because a single study using a dual imaging agent may be less expensive than two separate studies. Furthermore, the patient would save time because it would be expected that two studies using a dual imaging agent would take less time than two separate imaging studies using two different imaging agents.

Therefore, there is a need for a "dual" imaging agents that can be applied in the performance of more than one imaging modality. Description of any agent for use in dual imaging is very limited. See, e.g., U.S. Pat. No. 6,521,209 describing certain optically active magnetic resonance imaging agents, U.S. Pat. No. 6,770,259 pertaining to certain compositions that comprise a radiolabeled LTB4 binding agent and a radiolabeled perfusion imaging agent, and WO 2004/026344, describing agents that include a fluorescent dye and an MRI contrast agent. Thus, there is a need for novel imaging agents that can be used in concurrent imaging using more than one imaging modality.

Furthermore, in view of the epidemiological significance of cancer, there is the need for improved treatments. Chemotherapy and radiotherapy are treatment modalities that are commonly applied in the treatment of cancer. Compounds that can be administered to a subject that can provide for dual chemotherapy and radiation therapy ("radiochemotherapy") would provide a therapeutic advantage in terms of the dual targeting of a tumor following a single administration, and would also have other potential benefits such as greater patient convenience compared to standard treatment that would involve the application of two separate therapeutic modalities.

SUMMARY OF THE INVENTION

The inventors have synthesized certain novel chemical conjugates that can be applied as novel diagnostic and therapeutic agents. In general, these compounds include a backbone structure composed of two or more carbohydrate residues covalent attached to one another, to which are attached diagnostic and/or therapeutic moieties. The inventors have found that some of these compounds can applied in performing imaging studies using more than one imaging modality. For example, the dual agents can combine the dynamic imaging capabilities of standard CT (or MRI) imaging agents with PET (or SPECT) imaging agents. The saccharide backbone is non-toxic and binds to endothelial cells. Thus, the novel compounds have tumor-targeting capabilities. These novel agents are particularly beneficial in the imaging of focal lesions, such as tumors. There is improved resolution compared to either CT or MRI alone. Furthermore, with regard to imaging, these agents allow for the assessment of cellular function, including cellular viability. Thus, for example, the dual agents set forth herein can be applied in a wide variety of combinations of imaging modalities, including PET/CT, SPECT/CT, PET/MRI, SPECT/MRI, and optical imaging/MRI.

The inventors have also identified certain novel compounds that can be applied as agents to be used in the treatment of hyperproliferative disease such as cancer. In particular, compounds as set forth above that include a carbohydrate backbone can be combined with one or more therapeutic moieties that is a chemotherapeutic agent or an agent for use in radiotherapy, such as a beta-emitter or combination beta/gamma emitter. These novel compounds can also be applied in performing dual chemotherapy and imaging. Thus, the novel agents set forth herein allow for novel forms of cancer therapy and combined therapy and imaging.

The novel compounds of the present invention generally comprise the structure $X_1$—Y—$X_2$, wherein Y comprises two or more carbohydrate residues covalently attached to one another, $X_1$ and $X_2$ are diagnostic or therapeutic moieties covalently attached to Y, provided that when Y does not comprise two or more consecutive glucosamine residues, $X_1$ and $X_2$ are diagnostic moieties. Thus, as set forth above, the compounds set forth herein comprise a carbohydrate backbone that includes two or more carbohydrate residues, to which are attached two or more moieties that are diagnostic or therapeutic moieties. In some embodiments, $X_1$ and $X_2$ are both therapeutic moieties or both diagnostic moieties. In other embodiments, $X_1$ is a therapeutic moiety, and $X_2$ is a diagnostic moiety. The compounds set forth herein may comprise at least two therapeutic and/or diagnostic moieties, up to 10,000 or greater therapeutic or diagnostic moieties.

$X_1$ and $X_2$ may be attached to Y either covalently or ionically. In particular embodiments, $X_1$ and $X_2$ are covalently attached to Y. The binding, as described in greater detail below, may be attached to any moiety of Y. For example, attachment may be to a hydroxyl or amino group of one of the carbohydrate residues. Methods of conjugation of $X_1$ and $X_2$ to Y are by any methods known to those of ordinary skill in the art. Examples of such methods are described in the specification below.

The carbohydrate residues that comprise Y can be of any type of carbohydrate known to those of ordinary skill in the art. Examples include, but are not limited to, glucosamine, erythritol, erythrose, glycerol, ribose, deoxyribose, arabinose, glucose, mannose, galactose, fucose, mannose, N-acetylneuraminic acid, N-acetylglucosamine, and N-acetylgalactosamine. In particular embodiments, Y comprises two or more consecutive glucosamine residues (hereinafter, "poly(glucosamine)"). The compound can comprise any number of carbohydrate residues, such as from 2 to 2,000 or more residues. In more particular embodiments, the compound comprises 50 to 500 carbohydrate residues. Any number of additional residues or moieties may or may not be included in the chemical conjugates set forth herein. Thus, for example, a conjugate wherein Y is poly(glucosamine) may include any number of additional residues that are not glucosamine residues. Carbohydrate residues and additional chemical constituents are discussed in greater detail in the specification below.

The compounds set forth herein may include more than one $X_1$—Y—$X_2$ that are joined by covalent bonds between Y, such that the compound includes a polysaccharide backbone wherein the backbone comprises repeating Y units. The backbone may be straight or branched, linear or nonlinear. The number of repeating units may range from about 2 to about 2,000 or more units. In other examples, the number of repeating units ranges from about 50 to about 500.

Some of the compounds set forth herein further include a chelator moiety attached to Y. The attachment may be covalent or ionic. A chelator moiety is a molecule that comprises a combination of three to five atoms selected from the group consisting of nitrogen atoms, sulfur atoms, oxygen atoms and phosphorus atoms. Examples of such chelators include an $N_4$ compound, an $N_2S_2$ compound, DTPA, DMSA, EDTA, Cy-EDTA, EDTMP, DTPA, CyDTPA, Cy2DTPA, BOPTA, DTPA-MA, DTPA-BA, DTPMP, DOTA, TRITA, TETA, DOTMA, DOTA-MA, HP-DO3A, pNB-DOTA, DOTP, DOTMP, DOTEP, DOTPP, DOTBzP, DOTPME, HEDP, DTTP, an $N_3S$ triamidethiol (MAG3), DADS, MAMA, DADT, a diaminetetrathiol, an $N_2P_2$ dithiol-bisphosphine, a 6-hydrazinonicotinic acid, a propylene amine oxime, a tetraamine, a cyclal, and a cyclam. In particular embodiments, the chelator moiety is ethylenedicysteine.

The chelator may comprise from about 5% to about 50% by weight or greater of the compound. The diagnostic and/or therapeutic moieties may comprise from about 10% to about 50% by weight or more of the compound.

ments, for example, the imaging moiety is a contrast media, such as a CT contrast media, an MRI contrast media, and optical contrast media, and an ultrasound contrast media. Any CT contrast media is contemplated for inclusion in the compounds of the present invention. For example, the CT contrast media may be iothalamate, iohexol, diatrizoate, iopamidol, ethiodol, and iopanoate. In certain particular embodiments, the CT contrast media is diatrizoate. In some embodiments, the compound is of formula (II):

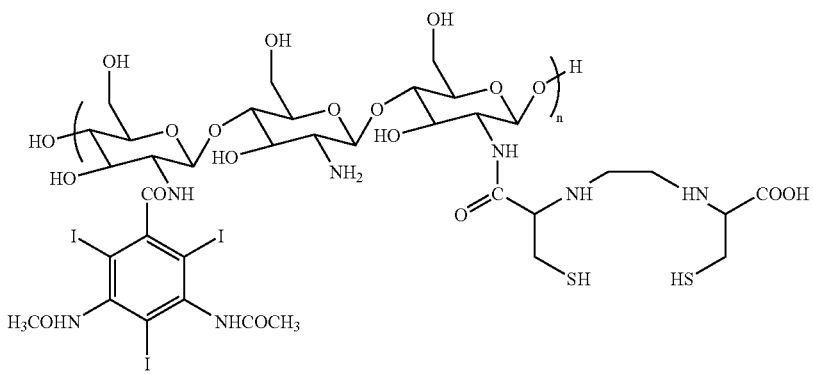

In some embodiments of the compounds of the present invention, the compound is of formula (I):

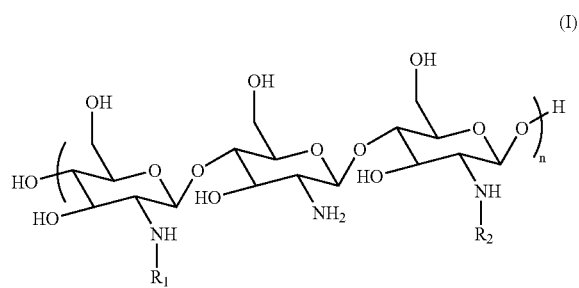

wherein $R_1$ is a therapeutic moiety or diagnostic moiety, $R_2$ is a chelator moiety; and wherein n is an integer that is one or greater; or a stereoisomer of (I), or a combination of stereoisomers of (I), or a pharmaceutically acceptable salt of (I).

In embodiments of the present compounds that include a chelator moiety, a valent metal ion may be attached to the chelator moiety. Any valent metal ion is contemplated for chelation to the compounds of the present invention. For example, the valent metal ion may be Tc-99m, Cu-60, Cu-61, Cu-62, Cu-67, In-111, Tl-201, Ga-67, Ga-68, As-72, Re-186, Re-188, Ho-166, Y-90, Sm-153, Sr-89, Gd-157, Bi-212, or Bi-213. In certain particular embodiments, the metal ion is either Re-188, Tc-99m, or Ga-68.

The diagnostic moieties of the present invention include any agent that can be applied in the performance of a test that is used to diagnose disease in a subject. In certain embodiments of the compounds of the present invention, the diagnostic moiety is an imaging moiety that is known or suspected to be of use in imaging studies. An imaging moiety include an agent that can be applied in the imaging of a cell or tissue, such as a tumor tissue in a subject. Imaging by any modality known to those of ordinary skill in the art is contemplated under this definition of imaging moiety. In certain embodiwherein n is an integer that is one or greater; or a stereoisomer of (II), or a combination of stereoisomers of (II), or a pharmaceutically acceptable salt of (II). Similarly, any MRI contrast media is contemplated for inclusion in the compounds of the present invention. For example, the MRI contrast media may be a gadolinium chelate, a manganese chelate, a chromium chelate, or iron particles. In some embodiments, the gadolinium chelate is Gd-DOTA. In some embodiments, the manganese chelate is Mn-DPDP. In some embodiments, the chromium chelate is Cr-DEHIDA.

Optical contrast media is can also be employed as diagnostic agents in the compounds of the present invention. For example, the optical contrast media may be fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, or dapoxyl dye. Any ultrasound contrast media known to those of ordinary skill in the art is contemplated for inclusion in the compounds of the present invention. For example, the ultrasound contrast media may be a perfluorinated agent, such as perfluorine or an analog of perfluorine. Any perfluorinated agent that is of use as an ultrasound contrast media is contemplated for inclusion in the present compounds.

Regarding therapeutic moieties, any therapeutic agent that can be applied in the treatment or prevention of disease in a subject is contemplated for use as a therapeutic moiety in the compounds of the present invention. For example, the therapeutic moiety may be an anti-cancer agent, such as a chelator capable of chelating to a therapeutic radiometallic substance, methotrexate, epipodophyllotoxin, vincristine, docetaxel, paclitaxel, daunomycin, doxorubicin, mitoxantrone, topotecan, bleomycin, gemcitabine, fludarabine, or 5-FUDR. In certain particular embodiments, the anti-cancer moiety is methotrexate. In some embodiments, the compound is of formula (III):

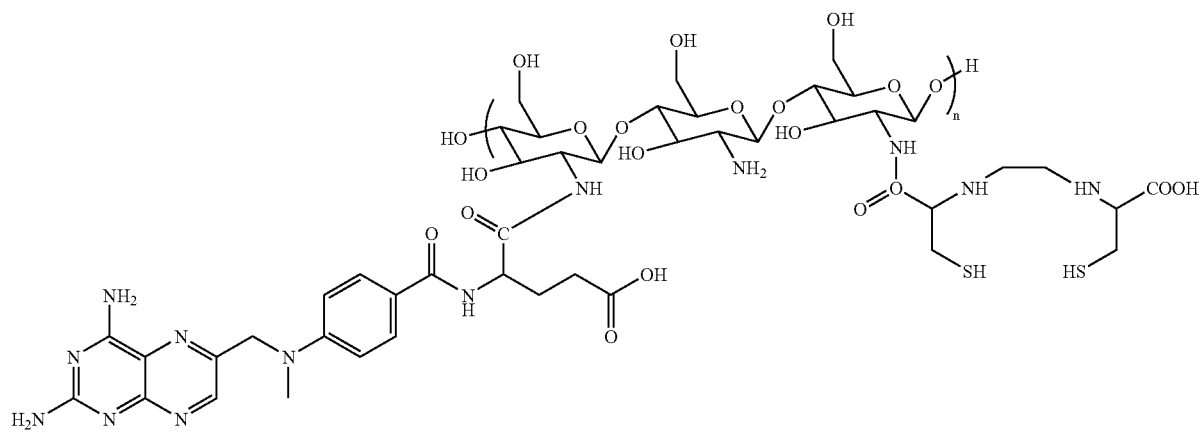

wherein n is an integer of one or greater; or a stereoisomer of (III), or a combination of stereoisomers of (III), or a pharmaceutically acceptable salt of (III).

The anti-cancer moiety may be a chelator moiety, such as a chelator that is capable of chelating to a therapeutic radiometallic substance selected from the group consisting of Re-188, Re-186, Ho-166, Y-90, Sr-89, Sm-153. The chelator may be capable of chelating to a therapeutic metal selected from the group consisting of arsenic, cobolt, copper, selenium, thallium and platinum.

Any of the compounds of the present invention set forth herein may further include a tissue-targeting moiety that can target the compound to a particular cell or tissue type following administration. Any agent that can make contact with a tissue, such as ligand-receptor binding, is contemplated as a tissue-targeting moiety. In some embodiments, the tissue-targeting moiety is a targeting ligand. For example, the targeting ligand may be as a disease cell cycle targeting compound, an antimetabolite, a bioreductive agent, a signal transductive therapeutic agent, a cell cycle specific agent, a tumor angiogenesis targeting ligand, a tumor apoptosis targeting ligand, a disease receptor targeting ligand, a drug-based ligand, an antimicrobial, a tumor hypoxia targeting ligand, an agent that mimics glucose, amifostine, angiostatin, an EGF receptor ligand, monoclonal antibody C225, monoclonal antibody CD31, monoclonal antibody CD40, capecitabine, a COX-2 inhibitor, deoxycytidine, fullerene, herceptin, human serum albumin, lactose, leuteinizing hormone, pyridoxal, quinazoline, thalidomide, transferrin, or trimethyl lysine. In other embodiments, the tissue-targeting moiety is an antibody, such as a monoclonal antibody C225, monoclonal antibody CD31, or monoclonal antibody CD40. Examples of these moieties are discussed in greater detail in the specification below.

Other embodiments of the present invention generally pertain to methods of synthesizing a therapeutic or diagnostic agent that involve (a) obtaining a compound as set forth above, and (b) admixing the compound with a radionuclide and a reducing agent to obtain a radionuclide labeled derivative, wherein the compound forms a chelate with the radionuclide. Any reducing agent known to those of ordinary skill in the art can be applied in these methods. For example, the reducing agent can be a dithionite ion, a stannous ion, or a ferrous ion. Furthermore, any radionuclide known to those of ordinary skill in the art can be utilized in these methods of synthesis. Examples of radionuclides include Tc-99m, Cu-60, Cu-61, Cu-62, In-111, Tl-201, Ga-67, Ga-68, As-72, and Gd-157.

Additional methods of the present invention generally pertain to methods of synthesizing a radiolabeled therapeutic agent for dual chemotherapy and radiation therapy that involve (a) obtaining a compound in accordance with any of the compounds set forth above that include a therapeutic moiety or tissue-targeting moiety, and (b) admixing the compound with a radionuclide and a reducing agent to obtain a radionuclide labeled derivative, wherein the compound forms a chelate with the radionuclide. Any radionuclide known to those of ordinary skill in the art can be applied in these methods, including, for example, dithionite ion, stannous ion, or ferrous ion. Furthermore, as set forth above, any radionuclide can be included in these methods, including, for example, a radionuclide that is a beta-emitter or beta/gamma emitter selected from the group that includes Re-188, Re-186, Ho-166, Y-90, Sr-89, and Sm-153.

Additional embodiments of the present invention generally pertain to methods of imaging a subject using a first imaging modality and a second imaging modality, that include: (a) administering to the subject a composition comprising a diagnostically effective amount of a compound in accordance with any of the claims above that includes an imaging moiety and (b) performing imaging using a first imaging modality by detecting a first signal from the compound; and (c) performing imaging using a second imaging modality by detecting a second signal from the compound, wherein the first imaging modality and the second imaging modality are performed either concurrently or consecutively. Any imaging modality known to those of ordinary skill in the art is contemplated as an imaging modality to be applied in the present methods. For example, the imaging modalities can include PET, CT, SPECT, MRI, optical imaging, and ultrasound. Any combination of imaging modalities is contemplated for inclusion in the methods of the present invention. For example, the first and second imaging modalities can be PET and CT, SPECT and CT, PET and MRI, SPECT and CT, PET and MRI, SPECT and MRI, optical imaging and MRI, or PET and ultrasound, or SPECT and ultrasound.

Other embodiments of the present invention generally pertain to methods of treating a subject with a hyperproliferative disease, that include (a) obtaining a therapeutically effective amount of one of the compounds set forth above that include a therapeutic moiety or tissue-targeting moiety, and (b) administering to the subject a composition thata includes a therapeutically effective amount of the compound. Any type of subject is contemplated for inclusion in these methods, including small mammmals and humans. In certain embodiments, the subject is a human with cancer. The cancer can be any type of cancer, such as, for example, breast cancer, lung cancer, ovarian cancer, brain cancer, liver cancer, cervical cancer, colon cancer, renal cancer, skin cancer, head & neck cancer, bone cancer, esophageal cancer, bladder cancer, uterine cancer, stomach cancer, pancreatic cancer, testicular cancer, lymphoma, or leukemia. Additionally, these methods may further include a second anti-cancer treatment, such as, for example, surgery, chemotherapy with a second agent, immunotherapy, treatment with an additional form of radiation therapy, or gene therapy.

Additional embodiments of the present invention pertain to kits for preparing a diagnostic or therapeutic compound that involve: (a) a sealed container including a predetermined quantity of a compound in accordance with any of the compounds set forth above, and (b) a sufficient amount of a reducing agent. In certain embodiments, the kit further includes a radionuclide. Any radionuclide known to those of ordinary skill in the art to be suitable for imaging can be included in the kits of the present invention. For example, the radionuclide can be Tc-99m, Cu-60, Cu-61, Cu-62, Cu-67, In-111, Tl-201, Ga-67, Ga-68, As-72, Re-188, Ho-166, Y-90, Sm-153, Sr-89, Gd-157, Bi-212, or Bi-213. The kit may include additional components beyond those set forth herein. The kit may be a kit for preparing a compound suitable for dual imaging, a kit suitable for preparing a compound for chemotherapy, and/or a kit suitable for preparing a compound suitable for dual chemotherapy and radiation therapy.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
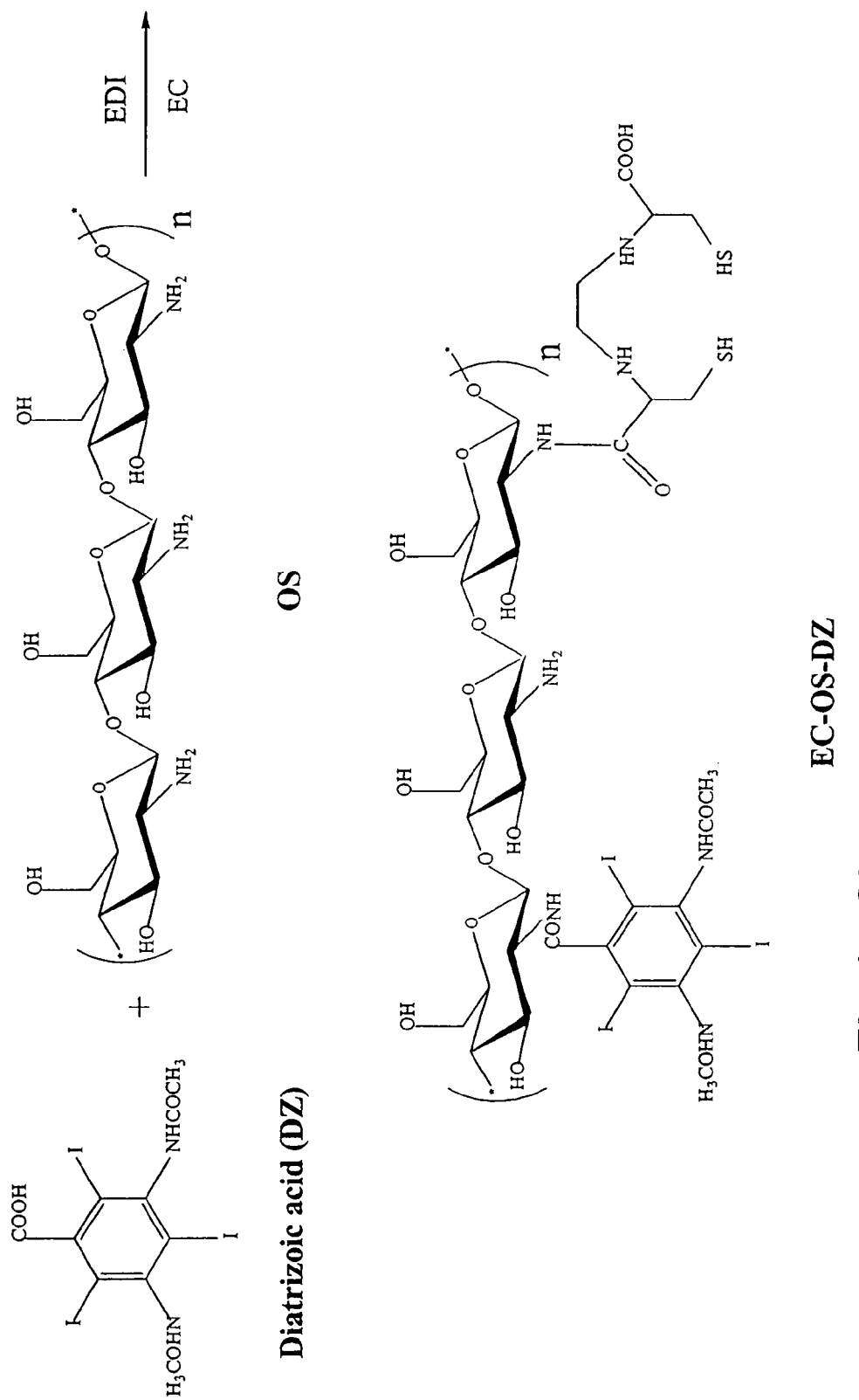
FIG. 1. Chemical synthesis of EC-OS-DZ.

The present invention provides for novel compounds that comprise oligosaccharides, such as poly(glucosamine), conjugated to a first moiety that is a chelator moiety and a second moiety that is a therapeutic moiety or diagnostic moiety. These compounds can be used to perform dual imaging, including, for example, PET/CT, SPECT/CT, PET/MRI, SPECT/MRI, and optical/MRI, or can be applied as agents for dual chemotherapy and radiation therapy. The therapeutic moiety can be any therapeutic agent, such as an anti-cancer agent. Also disclosed are methods of treating a subject with a hyperproliferative disease, such as cancer, using certain of these novel agents that comprise a therapeutic agent.

The present invention also provides for novel compounds that comprise an oligosaccharide conjugated to two moieties, wherein the moieties are diagnostic moieties. These compounds can also be used, as set forth herein, to perform dual imaging. Methods of synthesizing radiolabeled imaging agents for dual imaging and radiolabeled therapeutic agents for dual chemotherapy and radiation therapy are also disclosed, as well as kits for preparing these agents.

A. CARBOHYDRATES, SACCHARIDES, AND POLYSACCHARIDES

The present invention pertain to compounds that include a backbone composed of two or more carbohydrate residues covalent attached to one another, to which are attached diagnostic and/or therapeutic moieties. As used herein, the terms "saccharide" and "polysaccharide" pertain to any compound comprising two or more consecutive carbohydrate moieties, D-, L- or DL-configuration, wherein the carbohydrate residues are covalently linked to one another. The residues can be joined in a straight or branched configuration. In certain preferred embodiments of the present invention, the polysaccharide comprises a poly(glucosamine). As defined herein, poly (glucosamine) pertains to a molecule that comprises any number of glucosamine residues joined together by covalent bonds. The glucosamine residues can be in the D-, L-, or DL-configuration. For example, a poly(glucosamine), as set forth herein, may include 2 glucosamine residues that are covalently linked. In other embodiments, the (poly)glucosamine comprises about 3 to 10,000 or more glucosamine residues, or any number of glucosamine residues not specifically set forth herein.

Other examples of carbohydrate residues that are contemplated by the present invention include, but are not limited to, erythritol, erythrose, glycerol, ribose, deoxyribose, arabinose, glucose, mannose, galactose, fucose, mannose, N-acetylneuraminic acid, N-acetylglucosamine, and N-acetylgalactosamine. The linkage between carbohydrate residues and therapeutic or diagnostic moieties is alpha or beta.

The carbohydrates of the present invention may include optional substituents. Any substitution is contemplated by the compounds and methods of the present invention. Exemplary substitutions include hydrogen, hydroxyl, carboxyl, azido, cyano, alkyl, substituted alkyl, aryl, substituted aryl, alkenyl, substituted alkenyl, amine, amide, carboxyl, halogen, and thiol. The linkage between the carbohydrate residues of the carbohydrate and any optional substituent is alpha or beta. The substituents may be in the D-, L-, or DL-configuration.

Some embodiments of the compounds of the present invention include any number of "monomeric units." In the context of the present invention, a "monomeric unit" is defined as a small molecule that has the ability to become chemically bonded to another molecule. In some embodiments, the compounds of the present invention comprise a single monomeric unit. In other embodiments, the compounds of the present invention may comprise more than one monomeric unit chemically bonded to one another. In some embodiments, the compound comprises more than one monomeric unit joined by a covalent bond. A monomeric unit comprises two or more covalently attached carbohydrate moieties forming a backbone that is conjugated to a chelator and a drug moiety. In certain embodiments of the present invention, the carbohydrate backbone is a poly(glucosamine), as set forth above. In other embodiments, the carbohydrate backbone is chitin, chitosan, heparin, chondroitin, hyaluronate or an analog of one of these agents.

The monomeric units may be covalently bonded to one another. The monomeric units that are covalently bonded to one another may be the same, or may differ in certain respects, such as by the type of substituents, the location of substituents, configuration of bonds, the number of chelator moieties, the number of diagnostic moieties, or the number of therapeutic moieties that are bound to the monomeric unit. Certain compounds of the present invention may comprise between one monomeric unit and 10,000 monomeric units, or any greater number of monomeric units, or any number of monomeric units not specifically set forth herein. The compound can have any molecular weight. In certain embodiments of the present invention, the compound has a molecular weight of from about 3,000 daltons to about 50,000 daltons. In certain particular embodiments, the compound has a molecular weight of about 10,000 daltons.

The carbohydrate and chelator moiety may comprise any percentage weight of the compound. In certain embodiments, the carbohydrate and chelator moiety comprise about 5% to about 50% by weight of the compound. In some embodiments, the carbohydrate and chelator moiety comprise about 10% by weight of the compound.

B. CHELATOR MOIETIES

Some of the novel compounds set forth herein include one or more chelator moieties. The chelator moiety may be substituted at an amine moiety of the carbohydrate, or at any other residue of the carbohydrate. There may be one chelator moiety conjugated to the carbohydrate, or any greater number of chelator moieties conjugated to the carbohydrate.

The term "moiety" as used herein refers to a part of the compound of the present invention. The "chelating moiety" can be any chelating agent known to those of ordinary skill in the art. A "chelator" is any substance that binds particular ions. In certain embodiments, for example, the chelator moiety is EC. EC can be prepared in a two-step synthesis according to previously described methods (see Ratner and Clarke, 1937; Blondeau et al., 1967; each incorporated herein by reference). The precursor, L-thiazolidine-4-carboxylic acid, can be synthesized prior to preparing EC. The structure of EC can be confirmed by $^1$H-NMR and fast-atom bombardment mass spectroscopy (FAB-MS).

Other examples of chelator moieties include, but are not limited to, DTPA (diethylenetriamine pentaacetic acid); dimercaptosuccinic acid (DMSA); ethylenediaminetetraacetic acid (EDTA); 1,2-cyclohexanediamine-N,N,N',N'-tetraacetic acid (Cy-EDTA); ethylenediaminetetramethylenephosphonic acid (EDTMP); N-[2-[bis(carboxymethyl)amino]cyclohexyl]-N'-(carboxymethyl)-N,N-'-ethylenediglycine (CyDTPA); N,N-bis[2-[bis(carboxymethyl)amino]cyclohexylglycine (Cy.sub.2DTPA); 2,5,8-tris(carboxymethyl)-12-phenyl-11-oxa-2,5,8-triazadodecane-1,9-dicarboxylic acid (BOPTA); diethylenetriaminepentaacetic acid, monoamide (DTPA-MA); diethylenetriaminepentaacetic acid, biamide (DTPA-BA); diethylenetriamine-N,N,N',N",N"-pentamethylenephosphonic acid (DTPMP); tetraazacyclododecane-N,N',N",N"'-tetraacetic acid (DOTA); tetraazacyclotridecane-N,N',N",N"'-tetraacetic acid (TRITA); tetraazacyclotetradecane-N,N',N",N"'-tetraacetic acid (TETA); tetraazacyclododecane-.alpha.,.alpha.',.alpha.",.alpha.'"-tetramethyl-N,N',N",N"'-tetraacetic acid (DOTMA); tetraazacyclododecane-N,N',N",N"'-tetraacetic acid, monoamide (DOTA-MA); 10-(2-hydroxypropyl)-1,4,7,10-tetraazacyclododecane-1,4,7-triacetic acid (HP-DO3A); 1-((p-nitrophenyl)carboxymethyl)-4,7,10-tris(carboxymethyl)-1,4,7,10-tetraazacyclododecane (pNB-DOTA); tetraazacyclodecane-N,N',N",N"'-tekamethylenephosphonic acid (DOTP); tetraazacyclododecane-N,N',N",N"'-tetramethylenetetramethylphosphinic acid (DOTMP); tetraazacyclododecane-N,N',N",N"'-tetramethylenetetraethylphosphinic acid (DOTEP); tetraazacyclododecane-N,N',N",N"'-tetramethylenetetraphenylphosphinic acid (DOTPP); tetraazacyclododecane-N,N',N",N"'-tetramethylenetetrabenzylphosphinic acid (DOTBzP); tetraazacyclodecane-N,N',N",N-'"-tetramethylenephosphonic acid-P,P',P",P"'-tetraethyl ester (DOTPME); hydroxyethylidenediphosphonate (HEDP); diethylenetriaminetetramethylenephosphonic acid (DTTP); N.sub.3S triamidethiols (MAG3); N.sub.2S.sub.2 diamidedithiols (DADS); N.sub.2S.sub.2 monoamidemonoaminedithiols (MAMA); N.sub.2S.sub.2 diaminedithiols (DADT); N.sub.2S.sub.2 diaminedithiols acid (ethyleledicysteine, EC), N.sub.2S.sub.4 diaminetetrathiols; N.sub.2P.sub.2 dithiol-bisphosphines; 6-hydrazinonicotinic acids; propylene amine oximes; tetraamines; cyclals and cyclams. One of ordinary skill in the art would be familiar with the numerous agents that can be applied as chelator moieties in the context of the present invention.

The chelator moieties of the present invention may comprise a combination of any number of atoms selected from the group consisting of nitrogen atoms, sulfur atoms, oxygen atoms, and phosphorus atoms. In certain particular embodiments, the chelator moiety includes a combination of three to five such atoms. In some embodiments, the chelator is capable of chelating to any number of valent metal ions through coordination to other atoms, such as nitrogen atoms, sulfur atoms, oxygen atoms, and/or phosphorus atoms. In certain embodiments, the chelator is capable of chelating three to five valent metal ions. Any valent metal ion is contemplated for chelation to the chelators of the present invention. Examples of these valent metal ions include, but are not limited to, Tc-99m, Cu-60, Cu-61, Cu-62, In-111, Tl-201, Ga-67, and Ga-68.

In certain embodiments of the present invention, the dual radiochemotherapeutic and radiotherapeutic compounds of the present invention include chelator moieties wherein the chelator is capable of chelating to a beta-emitter or a dual beta/gamma emitter with a chemotherapeutic agent. Examples of beta emitters include Re-188, Re-186, Sr-89, Ho-166, Y-90, Sn-153, As-72. Examples of chemotherapeutic agents, which are discussed in greater detail below, include antimetabolites, apoptotic, bioreductive, signal transductive therapeutic, receptor responsive or cell cycle specific agent. One of ordinary skill in the art would be familiar with additional such beta emitters that can be applied to the delivery of radiotherapy, which is discussed in greater detail in other parts of this specification.

Information pertaining to the synthesis of EC conjugates and $N_2S_2$ conjugates is provided in U.S. Pat. No. 6,692,724, U.S. patent application Ser. No. 09/599,152, U.S. patent application Ser. No. 10/627,763, U.S. patent application Ser. No. 10/672,142, U.S. patent application Ser. No. 10/703,405, and U.S. patent application Ser. No. 10/732,919, each of which is herein specifically incorporated by reference in their entirety for this section of the specification and all other sections of the specification.

C. THERAPEUTIC MOIETIES

Certain embodiments of the present invention pertain to compounds comprising poly(glucosamine) conjugated to a first moiety that is a chelator moiety and a second moiety that is a therapeutic or diagnostic moiety. Regarding therapeutic moieties, any therapeutic agent known to those of ordinary skill in the art is contemplated as a "therapeutic moiety." A "therapeutic agent" is defined herein to include any compound or substance or drug that can be administered to a subject, or contacted with a cell or tissue, for the purpose of treating a disease or disorder, or preventing a disease or disorder, or treating or preventing an alteration or disruption of a normal physiologic process. For example, the therapeutic moiety may be an anti-cancer moiety, such as a chemotherapeutic agents.

Examples of anti-cancer moieties include any chemotherapeutic agent known to those of ordinary skill in the art. Examples of such chemotherapeutic agents include, but are not limited to, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristin, vinblastin and methotrexate, or any analog or derivative variant of the foregoing. In certain particular embodiments, the anti-cancer moiety is methotrexate and the chelating moiety is EC.

Additional examples of anticancer agents include those drugs of choice for cancer chemotherapy listed in Table 1:

TABLE 1

DRUGS OF CHOICE FOR CANCER CHEMOTHERAPY
The tables that follow list drugs used for treatment of cancer in the USA and Canada and their major adverse effects. The Drugs of Choice listing based on the opinions of Medical Letter consultants. Some drugs are listed for indications for which they have not been approved by the US Food and Drug Administration. Anticancer drugs and their adverse effects follow. For purposes of the present invention, these lists are meant to be exemplary and not exhaustive.

| DRUGS OF CHOICE | | |
|---|---|---|
| Cancer | Drugs of Choice | Some alternatives |
| Adrenocortical** | Mitotane | Doxorubicin, streptozocin, |
|  | Cisplatin | etoposide |
| Bladder* | Local: Instillation of BCG | Instillation of mitomycin, |
|  | Systemic: Methotrexate + vinblastine + doxorubicin + claplatin | doxorubicin or thiotape |
|  | (MVAC) | Pecitaxel, substitution of |
|  | Claplatin + Methotrexate + vinblastine | carboplatin for claplatin in |
|  | (CMV) | combinations |
| Brain | | |
| Anaplastic astrocytoma* | Procarbazine + lamuatine + vincristine | Carmustine, Claplatin |
| Anaplastic oligodendro-Giloma* | Procarbazine + lamustine + vincristine | Carmustine, Claplatin |
| Gilabiastome** | Carmustine or lamustine | Procarbazine, claplatin |
| Medulloblastoma | Vincristine + carmustine ± mechiorethamine ± methotrexate | Etoposide |
|  | Mechiorethamine + vincristine + procarbazine + prednisone (MOPP) | |
|  | Vincristine + claplatin ± cyclophosphamide | |
| Primary central nervous system lymphoma | Methotrexate (high dose Intravenous and/or Intrathecal) ± cytarabine (Intravenous and/or Intrathecal) | |
|  | Cyclophosphamide + Doxorubicin + vincristine + prednisone (CHOP) | |
| Breast | Adjuvant[1]: Cyclophosphamide + methotrexate + fluorouracil (CMF); | |
|  | Cyclophosphamide + Doxorubicin ± fluorouracil (AC or CAF); Tamoxifen | |
|  | Metastatic: Cyclophosphamide + methotrexate + fluorouracil (CMF) or | Paclitaxel; thiotepa + Doxorubicin + vin-blastine; mitomycin + |
|  | Cyclophosphamide + duxorubicin ± fluorouracil (AC or CAF) for receptor-negative and/or hormone-refractory; | vinblastine; mitomycin + methotrexate + mitoxantrone; fluorouracil by continuous infusion; Bone |
|  | Tamoxifen for receptor-positive and/or hormone-sensitive[2] | marrow transplant[3] |

TABLE 1-continued

| | | |
|---|---|---|
| Cervix** | Claplatin<br>Ifosfamide with means<br>Bleomycin + ifosfamide with means + claplatin | Chlorambucil, vincristine,<br>fluorouracil, Doxorubicin,<br>methotrexate, altretamine |
| Chorlocarcinoma | Methotrexate ± leucovorin<br>Dactinomycin | Methotrexate + dactinomycin +<br>cyclophosphamide (MAC)<br>Etoposide + methotrexate +<br>dactinomycin + cyclophosphamide +<br>vincristine |
| Colorectal* | Adjuvant colon[4]: Fluorouracil + levam-isole;<br>fluorouracil + leucovorin<br>Metastatic: fluorouracil + leucovorin | Hepatic metastases:<br>Intrahepatic-arterial floxuridine<br>Mitomycin |
| Embryonal rhabdomyosar-coma[5] | Vincristine + dectinomycin ± cyclophasphamide<br>Vincristine + ifosfamide with means + etoposide | Same + Doxorubicin |
| Endometrial** | Megastrol or another progestin<br>Doxorubicin + claplatin ± cyclophosphamide | fluorouracil, tamoxifen,<br>altretamine |
| Esophageal* | Claplatin + fluorouracil | Doxorubicin, methotraxate,<br>mitomycin |
| Ewing's sarcoma[5] | Cyclophosphamide (or ifosfamide with<br>means) + Doxorubicin + vincristine (CAV) ± dactinomycin | CAV + etoposide |
| Gastric** | Fluorouracil ± leucavorin | Claplatin Doxorubicin,<br>etoposide, methotrexate + leucovorin,<br>mitomycin |
| Head and neck squambus cell*[6] | Claplatin + fluorouracil<br>Methotrexate | Blomycin, carboplatin, paclitaxel |
| Islet cell** | Streptozocin + Doxorubicin | Streptozocin + fluorouracil;<br>chlorozotocin[†]; octreotide |
| Kaposi's sarcoma*<br>(Aids-related) | Etoposide or interferon alfa or vinblastine<br>Doxorubicin + bleomycin + vincristine or<br>vinblastine (ABV) | Vincristine, Doxorubicin,<br>bleomycin |
| Leukemia | | |
| Acute lymphocytic leukemia (ALL)[7] | Induction: Vincristine + prednisone + asparaginase ± daunorubicin<br>CNS prophylaxis: Intrathecal methotrexate ± systemic<br>high-dose methotrexate with<br>leutovorin ± Intrathecal cytarabine ± Intrathecal<br>hydrocortisone<br><br>Maintenance: Methotrexate + mercaptopurine<br>Bone marrow transplant.[3 8] | Induction: same ± high-dose<br>methotrexate ± cyterabine;<br>pegaspargase instead of<br>asparaginese<br>Teniposide or etoposide<br>High-does cytarabine<br>Maintenance: same + periodic<br>vincristine + prednisone |
| Acute myeloid leukemia (AML)[9] | Induction: Cytsrabine + either daunorubicin<br>or idarubicin<br>Post Induction: High-dose cytarabine ± other<br>drugs such as etoposide<br>Bone marrow transplant[3]. | Cytarabine + mitoxentrone<br>High-dose cyterabine |
| Chronic lymphocytic leukemia (CLL) | Chlorambucil ± prednisone<br>Fludarabin | Cladribine, cyclophosphamide,<br>pentostatin, vincristine,<br>Doxorubicin |
| Chronic myeloid leukemia (CML)[10] | | |
| Chronic phase | Bone marrow transplant[3]<br>Interferon alfa<br>Hydroxyures | Busulfan |
| Accelerated[11] | Bone marrow transplant[3] | Hydroxyures, busulfen |
| Blast crisis[11] | Lymphoid: Vincristine + prednisone + L-<br>separaginess + intrathecal methotrexate (± maintenance<br>with methotrexate + 8-<br>marcaptopurine) | Tretinoln[†]<br>Amsecrine, [†]azacitidine<br>Vincristine ± plicamycin |
| Hairy cell Leukemia | Pentostatin or cladribine | Interferon alfa, chlorambucil,<br>fludarabin |
| Liver** | Doxorubicin<br>Fluorouracil | Intrahepatic-arterial floxuridine<br>or claplatin |
| Lung, small cell (cat cell) | Claplatin + etoposide (PE)<br>Cyclophosphamide + doxorubicin + vincristine (CAV)<br>PE alternated with CAV<br>Cyclophosphamide + etoposide + claplatin (CEP)<br>Duxorubicin + cyclophosphamide + etoposide (ACE) | Ifosfamide with means +<br>carboplatin + etoposide (ICE)<br>Daily oral etoposide<br>Etoposide + ifosfamide with<br>means + claplatin (VIP<br>Paclitaxel |
| Lung (non-small cell)** | Claplatin + etoposide<br>Claplatin + Vinblastine ± mitomycin<br>Claplatin + vincrisine | Claplatin + fluorouracil + leucovorin<br>Carboplatin + paclitaxel |

TABLE 1-continued

Lymphomas

| | | |
|---|---|---|
| Hodgkin's[12] | Doxorubicin + bleomycin + vinblastine + dacarbazine (ABVD)<br>ABVD alternated with MOPP<br>Mechlorethamine + vincristine + procarbazine (± prednisone) + doxorubicin + bleomycin + vinblastine (MOP[P]-ABV) | Mechlorethamine + vincristine + procarbazine + prednisone (MOPP)<br>Chlorambusil + vinblastine +<br>Etoposide + vinblastine + doxorubicin procarbazine + prednisone ±carmustine Bone marrow transplant[3] |

Non-Hodgkin's

| | | |
|---|---|---|
| Burkitt's lymphoma | Cyclophosphamide + vincristine + methotrexate<br>Cyclophosphamide + high-dose cytarabine ± methotrexate with leutovorin<br>Intrathecal methotrexate or cytarabine | Ifosfamide with means<br>Cyclophosphamide + doxorubicin + vincrletine + prednisone (CHOP) |
| Difuse large-cell lymphoma | Cyclophosphamide + doxorubicin + vincristine + prednisone (CHOP) | Dexamethasone sometimes substituted for prednisone<br>Other combination regimens, which may include methotrexate, etoposide, cytarabine, bleomycin, procarbazine, ifosfamide and mitoxantrone<br>Bone marrow transplant[3] |
| Follicular lymphoma | Cyclophosphamide or chlorambusil | Same ± vincristine and prednisone, ± etoposide<br>Interferon alfa, cladribine, fludarabin<br>Bone marrow transplant[3]<br>Cyclophosphamide + doxorubicin + vincristine + prednisone (CHOP) |
| Melanoma** | Interferon Alfa<br>Dacarbazine | Carmustine, lomustine, cisplatin<br>Dacarbazine + clapletin + carmustine + tamoxifen Aldesleukin |
| Mycosis fungoides* | PUVA (psoralen + ultraviolet A)<br>Mechlorethamine (topical)<br>Interferon alfa<br>Electron beam radiotherapy<br>Methotrexate | Isotretinoin, topical carmustine, pentosistin, fludarabin, cladribine, photopheresis (extra-corporeal photochemitherapy), chemotherapy as in non-Hodgkin's lymphoma |
| Mysloma* | Melphelan (or cyclophosphamide) + prednisons<br>Melphalan ± carmustine + cyclophosphamide + prednisons + vincristine<br>Dexamethasone + doxorubicin + vincristine (VAD)<br>Vincristine + carmustine + doxorubicin + prednisons (VBAP) | Interferon alfa<br>Bone marrow transplant[3]<br>High-dose dexamethasons |
| Neuroblestoma* | Doxorubicin + cyclophosphamide + claplatin + teniposide or etoposide<br>doxorubicin + cyclophosphamide<br>Claplatin + cyclophosphamide | Carboplatin, etoposide<br>Bone marrow transplant[3] |
| Osteogenic sarcoma[5] | Doxorubicin + claplatin ± etopside ± ifosfamide | Ifosfamide with means, etoposide, carboplatin, high-dose methotrexate with leucovorin<br>Cyclophosphamide + etoposide |
| Ovary | Claplatin (or carboplatin) + paclitaxel<br>Claplatin (or carboplatin) + cyclophosphamide (CP) ± doxorubicin (CAP) | Ifosfamide with means, paclitaxel, tamoxifen, melphalan, altretamine |
| Pancreatic** | Fluoroutacil ± leucovorin | Gemoltabinet |
| Prostate | Leuprolide (or goserelln) ± flutamide | Estramustine ± vinblastine, aminoglutetimide + hydrocortleone, estramustine + etoposide, diethylstllbestrol, nilutamide |
| Renal** | Aldesleukin<br>Inteferon alfa | Vinblastine, floxuridine |
| Retinoblestoma[5]* | Doxorubicin + cyclophosphamide ± claplatin ± etoposide ± vincristina | Carboplatin, etoposide, Ifosfamide with means |
| Sarcomas, soft tissue, adult* | Doxorubicin ± decarbazine ± cyclophosphamide ± Ifosfamide with means | Mitornyeln + doxorubicin + claplatin Vincristina, etoposide |

TABLE 1-continued

| | | |
|---|---|---|
| Testicular | Claplatin + etoposide ± bleomycin (PEB) | Vinblestine (or etoposide) + Ifosfamide with means + claplatin (VIP) Bone marrow transplant[3] |
| Wilms' tumor[5] | Dectinomycln + vincriatine ± doxorubicin ± cyclophosphamide | Ifosfamide with means, etoposide, carboplatin |

*Chemotherapy has only moderate activity.
**Chemotherapy has only minor activity.
[1]Tamoxifen with or without chemotherapy is generally recommended for postmenopausal estrogen-receptor-positive, mode-positive patients and chemotherapy with or without tamoxlfen for premenopausal mode-positive patients. Adjuvant treatment with chemotherapy and/or tamoxifen is recommended for mode-negative patients with larger tumors or other adverse prognostic indicators.
[2]Megastrol and other hormonal agents may be effective in some patients with tamoxifen fails.
[3]After high-dose chemotherapy (Medical Letter, 34: 79, 1982).
[4]For rectal cancer, postoperative adjuvant treatment with fluoroutacil plus radiation, preceded and followed by treatment with fluorouracil alone.
[5]Drugs have major activity only when combined with surgical resection, radiotherapy or both.
[6]The vitamin A analog lactratinoln (Acgutana) can control pre-neoplastic lesions (leukoplakla) and decreases the rate of second primary tumors (Banner et al, 1994).
[†]Available in the USA only for investigational use.
[7]High-risk patients (e.g., high counts, cytogenetic abnormalities, adults) may require additional drugs for induction, maintenance and "Intensificiation" (use of additional drugs after achievement of remission). Additional drugs include cyclophosphamida, mitoxantrone and thloguanine. The results of one large controlled trial in the United Kingdom suggest that Intensificiation may improve survival in all children with ALL (Chasselle et al, 1995).
[8]Patients with a poor prognosis initially or those who relapse after remission.
[9]Some patients with acute promyelocytic leukemia have had complete responses to tratinoin. Such treatment can cause a toxic syndrome characterized primarily by fever and respiratory distress (Warrell, Jr et al, 1993).
[10]Allogeheic HLA-identical sibling bone marrow transplantation can cure 40% to 70% of patients with CML in chronic phase, 18% to 28% of patients with accelerated phase CML, and <15% patients in blast crisis. Disease-free survival after bone marrow transplantations adversely influenced by age >50 years, duration of disease >3 years from diagnosis, and use of one-antigen-mismatched or matched-unrelated donor marrow. Interferon also may be curative in patients with chronic phase CML who achieve a complete cytogenetic response (about 10%); it is the treatment of choice for patents >80 years old with newly diagnosed chronic phase CML and for all patients who are not candidates for an allgensic bone marrow transplant. Chemotherapy alone is palliative.
[11]If a second chronic phase is achieved with any of these combinations, allogeneic bone marrow transplant should be considered. Bone marrow transplant in second chronic phase may be curative for 30% to 35% of patients with CML.
[12]Limited-stage Hodgkin's disease (stages 1 and 2) is curable by radiotherapy. Disseminated disease (stages 3b and 4) require chemotherapy. Some intermediate stages and selected clinical situations may benefit from both.
+ Available in the USA only for investigational use.

| ANTICANCER DRUGS AND HORMONES | | |
|---|---|---|
| Drug | Acute Toxicity‡ | Delayed toxicity‡ |
| Aldesleukin (Interleukin-2; Proleukin - Cetus Oncology) | Fever; fluid retention; hypertension; respiratory distress; rash; anemia; thrombocytophenia; nausea and vomiting; diarrhea; capillary leak syndrome; naphrotoxlolty; myocardialtoxicity; hepatotoxicity; erythernanodosum; neutrophil chemotactic defects | Neuropsychiatric disorders; hypothyrldiam; nephrotic syndrome; possibly acute leukoencaphalopathy; brachial plexopathy; bowel perforation |
| Altretamine (hexamethyl-melamine; Hexalen - U Bioscience) | Nausea and vomiting | Bone marrow depression; CNS depression; peripheral neuropathy; visual hallucinations; stexis; tremors, alopecia; rash |
| Aminogiutethimide (Cytadren - Ciba) | Drowsiness; nausea; dizziness; rash | Hypothryroidism (rare); bone marrow depression; fever; hypotension; mascullinization |
| †Amsacrine (m-AMSA; amaidine; AMSP P-D-Parke-Davis, Amsidyl-Warner-Lambert) | Nausea and vomiting; diarrhea; pain or phlebitis on infuelon; anaphylaxia | Bone marrow depression; hepactic injury; convulsions; stomatitle; ventricular fibrillation; alopecia; congestive heart failure; renal dysfunction |
| Asparaginase (Elspar-merck; Kidrolase in Canada) | Nausea and vomiting; fever; chills; headache; hypersensitivity, anaphylexia; abdominal pain; hyperglycemia leading to coma | CNS depression or hyperexcitability; acute hemorrhagic pancreatitis; coagulation defects; thromboals; renal damage; hepactic damage |
| Cervix** | Claplatin Ifosfamide with means Bleomycin patin Ifosfamide with means | Chlorambucil, vincristine, fluoroutacil, doxorubicin, methotrexete, altretamine |

TABLE 1-continued

| | | |
|---|---|---|
| Chorlocarcinoma | Methotrexete ± leucovorin | Methotrexete + dectinomycin + cyclophosphamide Dactinomyclin (MAC) Etoposide + methotrexate + dactinomycin + cyclophosphamide + vincrlatine |
| Colorectal* | Adjuvant colon[4]: Fluoroutacil + lavamleole; fluoroutacil + leucovarin<br>Metastatic: Fluoroutacil + leucvarin | Hepatic metastases:<br>Intrahepactic-arterial<br>floxuridine<br>Mitomyclin |
| Embryonal rhebdomyosarcoma[6] | Vincriatine + dectinomycin ± cyclophosphamide<br>Vincristine + Ifosfamide with means + etoposide | Same + doxorubicin |
| Endometrial** | Megastrol or another progeetin<br>Doxorubicin + claplatin ± cyclophosphamide | Fluoroutacil, tamoxifen, altretamine |
| Cancer | Drugs of Choice | Some alternatives |
| Esophageal* | Claplatin + Fluoroutacil | Doxorubicin, methotrexete, mitomycin |
| Ewing's sarcoma[5] | Cyclophosphamide (or ifosfamide with means) + doxorubicin + vincrietine (CAV) ± dectinomycin | CAV + etoposide |
| Gastric** | Fluoroutacil ± leucovoin | Claplatin, doxorubicin, etoposide, methotrexete + leucovorin, mitomycin |
| Head and neck squamous cell*[5] | Claplatin + fluoroutacil<br>Methotrexete | Blaonycin, carboplatin, paciltaxel |
| Islet call** | Streptozocin + doxorubicin | Streptozocln + fluoroutacil; chlorozotocin; actreatide |
| Kaposal's sercoma* (AIDS-related) | Etoposide or Interferon alfa or vinbleomycin stine<br>Doxorubicin + bleomycin + vincristine or vinbleomycin stine (ABV) | Vincristine, doxorubicin, bleomycln |
| Leukemias<br>Acute lymphocytic leukemia (ALL)[7] | Induction: Vincristine + prednisone + asparaginase ± daunorubieln<br>CNS prophylaxia; Intrathecal methotrexete ± systemic high-dose methotrexete with leucovorin ± Intrethecal cytarabine ± Intrathecal hydrocortisone<br>Maintenance: methotrexete ± mercaptopurine<br>Bone marrow transplant[3] | Industion: same ± high-dose methotrexete ± cyterabine; pegaspargase instead of aspareginese<br>Teniposide or etoposide<br>High-dose cytarabine<br>Maintenance: same + periodic vincristine + prednisone |
| Acute myeloid leukemia (AML)[9] | Induction: Cytarabine + either daunrublein or idarubieln<br>Post Induction: High-dose cytarabine ± other drugs such as etoposide<br>Bone marrow transplant[3] | Cytarabine + mitoxantrone<br>High-dose cytarabine |
| Chronic lymophocytic leukemia (CLL) | Chlorambuell ± prednisone<br>Fludarabin | Claplatin, cyclophosphamide, pentostatin, vinorlstine, doxorubicin |

†Available in the USA only for investigational use.
‡Dose-limiting effects are in bold type. Cutaneous reactions (sometimes severe), hyperpigmentation, and ocular toxicity have been reported with virtually all nonhormonal anticancer drugs. For adverse interactions with other drugs, see the Medical Letter Handbook of Adverse Drug Interactions, 1995.
[1]Available in the USA only for investigational use.
[2]Megestrol and other hormonal agents may be effective in some pateients when tamoxifen fails.
[3]After high-dose chemotherapy (Medical Letter, 34: 78, 1992).
[4]For rectal cancer, postoperative adjuvant treatment with fluoroutacil plus radiation, preceded and followed by treatment with fluoroutacil alone.
[5]Drugs have major activity only when combined with surgical resection, radiotherapy or both.
[6]The vitamin A analog isotretinoin (Accutane) can control pre-neoplastic isions (leukoplaka) and decreases the rats of second primary tumors (Senner et al., 1994).
[7]High-risk patients (e.g., high counts, cytogenetic abnormalities, adults) may require additional drugs for Induction, maintenance and "Intensification" (use of additional drugs after achievement of remission). Additional drugs include cyclophosphamide, mitoxantrone and thioguamine. The results of one large controlled trial in the United Kingdom suggest that intensilibation may improve survival in all children with ALL Chassella et al., 1995).
[8]Patients with a poor prognosis initially or those who relapse after remission
[9]Some patients with acute promyclocytic leukemia have had complete responses to tretinoin. Such treatment can cuase a toxic syndrome characterized primarily by fever and respiratory distress (Warrell, Jr et al. 1993).
[10]Allogenaic HLA Identical sibling bone marrow transplantation can cure 40% to 70% of patients with CML in chroni phase, 15% to 25% of patients with accelerated phase CML, and <15% patients in blast crisis. Disease-free survival after bone marrow transplantation is adversely influenced by age >50 years, duration of disease >3 years from diagnosis, and use of one antigen mismatched or matched-unrelated donor marrow. Inteferon alfa may be curative in patients with chronic phase CML who achieve a complete cytogenetic resonse (about 10%); It is the treatment of choices for patients >50 years old with newly diagnosed chronic phase CML and for all patients who are not candidates for an allogenic bone marrow transplant. Chemotherapy alone is palliative.

D. DIAGNOSTIC MOIETIES

In certain particular embodiments of the present invention, the compounds of the present invention include a diagnostic moiety.

Any diagnostic agent known to those of ordinary skill in the art is contemplated as an imaging moiety. A "moiety" is defined herein to be a part of a molecule. As defined herein, a "diagnostic moiety" is a part of a molecule that is a chemical or compound that can be administered to a subject or contacted with a tissue for the purpose of performing a test that can facilitate the diagnosis of a disease in a subject, or condition associated with abnormal cell physiology. One example of a diagnostic moiety would be an imaging moiety. As defined herein, an "imaging moiety" is a part of a molecule that is a agent or compound that can be administered to a subject, contacted with a tissue, or applied to a cell for the purpose of facilitating visualization of particular characteristics or aspects of the subject, tissue, or cell through the use of an imaging modality. Imaging modalities are discussed in greater detail below. Any imaging agent known to those of ordinary skill in the art is contemplated as an imaging moiety of the present invention.

In certain embodiments, the imaging moiety is a contrast media. Examples include CT contrast media, MRI contrast media, optical contrast media, ultrasound contrast media, or any other contrast media to be used in any other form of imaging modality known to those of ordinary skill in the art. Particular specific examples of these contrast media are set forth above in the background section and summary of the invention, which is specifically incorporated into this section. Examples include diatrizoate (a CT contrast agent), a gadolinium chelate (an MRI contrast agent), and sodium fluorescein (an optical contrast media).

E. TISSUE-TARGETING MOIETIES

Some of the compounds of the present invention further comprise a tissue-targeting moiety. A "tissue-targeting moiety" is defined herein to refer to a part of a molecule that can bind or attach to tissue. The binding may be by any mechanism of binding known to those of ordinary skill in the art. Examples include antimetabolites, apoptotic agents, bioreductive agents, signal transductive therapeutic agents, receptor responsive agents, or cell cycle specific agents. The tissue may be any type of tissue, such as a cell. For example, the cell may be the cell of a subject, a cancer cell, or a bacterium.

In some embodiments the tissue-targeting moiety is a "targeting ligand." A "targeting ligand" is defined herein to be a molecule or part of a molecule that binds with specificity to another molecule. Any targeting ligand known to those of ordinary skill in the art is contemplated for inclusion as a targeting ligand that is to be included in the targeting ligands of the present invention.

Examples of targeting ligands include disease cell cycle targeting compounds, tumor angiogenesis targeting ligands, tumor apoptosis targeting ligands, disease receptor targeting ligands, drug-based ligands, antimicrobials, tumor hypoxia targeting ligands, an agent that mimics glucose, amifostine, angiostatin, EGF receptor ligands, capecitabine, COX-2 inhibitors, deoxycytidine, fullerene, herceptin, human serum albumin, lactose, leuteinizing hormone, pyridoxal, quinazoline, thalidomide, transferrin, and trimethyl lysine.

In further embodiments of the present invention, the tissue-targeting moiety is an antibody. Any antibody is contemplated as a tissue-targeting moiety in the context of the present invention. For example, the antibody may be a monoclonal antibody. One of ordinary skill in the art would be familiar with monoclonal antibodies, methods of preparation of monoclonal antibodies, and methods of use of monoclonal antibodies as ligands. In certain embodiments of the present invention, the monoclonal antibody is an antibody directed against a tumor marker. In some embodiments, the monoclonal antibody is monoclonal antibody C225, monoclonal antibody CD31, or monoclonal antibody CD40.

The compounds of the present invention may include a single tissue-targeting moiety, or more than one such tissue-targeting moiety. The tissue-targeting moiety may or may not be covalently bonded to the carbohydrate backbone of the compounds of the present invention. The tissue-targeting moiety may be bound to amine moiety, a hydroxyl moiety, or any other moiety of the compounds of the present invention. One of ordinary skill in the art would be familiar with the chemistry of these agents, and methods to incorporate these agents as moieties of the compounds of the claimed invention. Methods of synthesis of the compounds of the present invention are discussed in detail below.

Information pertaining to tissue targeting moieties and conjugation with compounds and chelators are provided in U.S. Pat. No. 6,692,724, U.S. patent application Ser. No. 09/599,152, U.S. patent application Ser. No. 10/627,763, U.S. patent application Ser. No. 10/672,142, U.S. patent application Ser. No. 10/703,405, U.S. patent application Ser. No. 10/732,919, each of which is herein specifically incorporated by reference in their entirety for this section of the specification and all other sections of the specification.

Representative examples of tissue-targeting moieties are discussed below.

1. Disease Cell Cycle Targeting Compounds

Disease cell cycle targeting refers to targeting of agents that are upregulated in proliferating cells. "Disease cell cycle targeting compounds" are compounds that are used to measure agents that are upregulated or downregulated in proliferating cells. For example, the cells may be cancer cells. Compounds used for this purpose can be used to measure various parameters in cells, such as tumor cell DNA content.

Many of these agents are nucleoside analogues. For example, pyrimidine nucleoside (e.g., 2'-fluoro-2'-deoxy-5-iodo-1-β-D-arabinofuranosyluracil [FIAU], 2'-fluoro-2'-deoxy-5-iodo-1-β-D-ribofuranosyl-uracil [FIAU], 2'-fluoro-2'-5-methyl-1-β-D-arabinofuranosyluracil [FMAU], 2'-fluoro-2'-deoxy-5-iodovinyl-1-β-D-ribofuranosyluracil [IVFRU]) and acycloguanosine: 9-[(2-hydroxy-1-(hydroxymethyl)ethoxy)methyl]guanine (GCV) and 9-[4-hydroxy-3-(hydroxymethyl)butyl]guanine (PCV) (Tjuvajev et al., 2002; Gambhir et al., 1998; Gambhir et al., 1999) and other $^{18}$F-labeled acycloguanosine analogs, such as 8-fluoro-9-[(2-hydroxy-1-(hydroxymethyl)ethoxy)methyl]guanine (FGCV) (Gambhir et al., 1999; Namavari et al., 2000), 8-fluoro-9-[4-hydroxy-3-(hydroxymethyl)butyl]guanine (FPCV) (Gambhir et al., 2000; Iyer et al., 2001), 9-[3-fluoro-1-hydroxy-2-propoxy methyl]guanine (FHPG) (Alauddin et al., 1996; Alauddin et al., 1999), and 9-[4-fluoro-3-(hydroxymethyl)butyl]guanine (FHBG) (Alauddin and Conti, 1998; Yaghoubi et al., 2001) have been developed as reporter substrates for imaging wild-type and mutant (Gambhir et al., 2000) HSV1-tk expression. Particular embodiments of the compounds of the present invention include adenosine and penciclovir (guanine) as the disease cell cycle targeting ligand. One or ordinary skill in the art would be familiar with these and other agents that are used for disease cell cycle targeting.

2. Angiogenesis Targeting Ligands

"Angiogenesis targeting ligands" refers to agents that can bind to neovascularization, such as neovascularization of tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose.

Throughout this application, "tumor angiogenesis targeting" refers to the use of an agent to bind to tumor neovascularization and tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. A tumor angiogenesis targeting ligand is a ligand that is used for the purpose of tumor angiogenesis targeting as defined above. Examples include COX-2 inhibitors, anti-EGF receptor ligands, herceptin, angiostatin, C225, and thalidomide. COX-2 inhibitors include, for example, celecoxib, rofecoxib, etoricoxib, and analogs of these agents.

3. Tumor Apoptosis Targeting Ligands

"Tumor apoptosis targeting" refers to use of an agent to bind to a cell that is undergoing apoptosis or at risk of undergoing apoptosis. These agents are generally used to provide an indicator of the extent or risk of apoptosis, or programmed cell death, in a population of cells, such as a tumor. One of ordinary skill in the art would be familiar with agents that are used for this purpose. A "tumor apoptosis targeting ligand" is a ligand that is capable of performing "tumor apoptosis targeting" as defined in this paragraph. The targeting ligand of the present invention may include TRAIL (TNF-related apoptosis inducing ligand) monoclonal antibody. TRAIL is a member of the tumor necrosis factor ligand family that rapidly induces apoptosis in a variety of transformed cell lines. The targeting ligand of the present invention may also comprise a substrate of caspase-3, such as peptide or polypeptide that includes the 4 amino acid sequence aspartic acid-glutamic acid-valine-aspartic acid. caspase-3 substrate (for example, a peptide or polypeptide that includes the amino acid sequence aspartic acid-glutamic acid-valine-aspartic acid), and any member of the Bcl family. Examples of Bcl family members include, for example, Bax, Bcl-xL, Bid, Bad, Bak, and Bcl-2). One of ordinary skill in the art would be familiar with the Bcl family, and their respective substrates.

Apoptosis suppressors are targets for drug discovery, with the idea of abrogating their cytoprotective functions and restoring apoptosis sensitivity to tumor cells (Reed, 2003).

4. Disease Receptor Targeting Ligands

In "disease receptor targeting," certain agents are exploited for their ability to bind to certain cellular receptors that are overexpressed in disease states, such as cancer. Examples of such receptors which are targeted include estrogen receptors, androgen receptors, pituitary receptors, transferrin receptors, and progesterone receptors. Examples of agents that can be applied in disease-receptor targeting include androgen, estrogen, somatostatin, progesterone, transferrin, luteinizing hormone, and luteinizing hormone antibody.

The radiolabeled ligands, such as pentetreotide, octreotide, transferrin, and pituitary peptide, bind to cell receptors, some of which are overexpressed on certain cells. Since these ligands are not immunogenic and are cleared quickly from the plasma, receptor imaging would seem to be more promising compared to antibody imaging.

The folate receptor is included herein as another example of a disease receptor. Folate receptors (FRs) are overexposed on many neoplastic cell types (e.g., lung, breast, ovarian, cervical, colorectal, nasopharyngeal, renal adenocarcinomas, malign melanoma and ependymomas), but primarily expressed only several normal differentiated tissues (e.g., choroid plexus, placenta, thyroid and kidney) (Orr et al., 1995; Weitman et al., 1992a; Campbell et al., 1991; Weitman et al., 1992b; Holm et al., 1994; Ross et al., 1994; Franklin et al., 1994; Weitman et al., 1994). FRs have been used to deliver folate-conjugated protein toxins, drug/antisense oligonucleotides and liposomes into tumor cells overexpressing the folate receptors (Ginobbi et al., 1997; Leamon and Low, 1991; Leamon and Low, 1992; Leamon et al., 1993; Lee and Low, 1994). Furthermore, bispecific antibodies that contain anti-FR antibodies linked to anti-T cell receptor antibodies have been used to target T cells to FR-positive tumor cells and are currently in clinical trials for ovarian carcinomas (Canevari et al., 1993; Bolhuis et al., 1992; Patrick et al., 1997; Coney et al., 1994; Kranz et al., 1995).

Examples of folate receptor targeting ligands include folic acid and analogs of folic acid. Preferred folate receptor targeting ligands include folate, methotrexate and tomudex. Folic acid as well as antifolates such as methotrexate enter into cells via high affinity folate receptors (glycosylphosphatidylinositol-linked membrane folate-binding protein) in addition to classical reduced-folate carrier system (Westerhof et al., 1991; Orr et al., 1995; Hsueh and Dolnick, 1993).

5. Drug Assessment

Certain drug-based ligands can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Examples of drug-based ligands include carnitine and puromycin.

6. Antimicrobials

Any antimicrobial is contemplated for inclusion as a targeting ligand. Preferred antimicrobials include ampicillin, amoxicillin, penicillin, cephalosporin, clidamycin, gentamycin, kanamycin, neomycin, natamycin, nafcillin, rifampin, tetracyclin, vancomycin, bleomycin, and doxycyclin for gram positive and negative bacteria and amphotericin B, amantadine, nystatin, ketoconazole, polymycin, acyclovir, and ganciclovir for fungi. One of ordinary skill in the art would be familiar with the various agents that are considered to be antimicrobials.

7. Agents that Mimic Glucose

Agents that mimic glucose are also contemplated for inclusion as targeting ligands. Preferred agents that mimic glucose, or carbohydrates, include neomycin, kanamycin, gentamycin, paromycin, amikacin, tobramycin, netilmicin, ribostamycin, sisomicin, micromicin, lividomycin, dibekacin, isepamicin, astromicin, aminoglycosides, glucose or glucosamine.

8. Tumor Hypoxia Targeting Ligands

In some embodiments of the present invention, the targeting ligand is a tumor hypoxia targeting ligand. Tumor cells are more sensitive to conventional radiation in the presence of oxygen than in its absence; even a small percentage of hypoxic cells within a tumor could limit the response to radiation (Hall, 1988; Bush et al., 1978; Gray et al., 1958). Hypoxic radioresistance has been demonstrated in many animal tumors but only in few tumor types in humans (Dische, 1991; Gatenby et al., 1988; Nordsmark et al., 1996). The occurrence of hypoxia in human tumors, in most cases, has been inferred from histology findings and from animal tumor studies. In vivo demonstration of hypoxia requires tissue measurements with oxygen electrodes and the invasiveness of these techniques has limited their clinical application.

Misonidazole, an example of a tumor hypoxia targeting ligand, is a hypoxic cell sensitizer, and labeling MISO with different radioisotopes (e.g., $^{18}$F, $^{123}$I, $^{99m}$Tc) may be useful for differentiating a hypoxic but metabolically active tumor from a well-oxygenated active tumor by PET or planar scintigraphy. [$^{18}$F]Fluoromisonidazole (FMISO) has been used with PET to evaluate tumors hypoxia. Recent studies have shown that PET, with its ability to monitor cell oxygen content through [$^{18}$F]FMISO, has a high potential to predict tumor response to radiation (Koh et al., 1992; Valk et al., 1992; Martin et al., 1989; Rasey et al., 1989; Rasey et al., 1990; Yang et al., 1995). PET gives higher resolution without collimation, however, the cost of using PET isotopes in a clinical setting is prohibitive.

F. VALENT METAL IONS AND RADIONUCLIDES

A variety of valent metal ions, or radionuclides, are known to be useful for radioimaging. Examples include $^{67}$Ga, $^{68}$Ga, $^{99m}$Tc, $^{111}$In, $^{123}$I, $^{125}$I, $^{131}$I, $^{169}$Yb, $^{60}$Cu, $^{61}$Cu, $^{62}$Cu, $^{201}$Tl, $^{72}$A, and $^{157}$Gd. Due to better imaging characteristics and lower price, attempts have been made to replace the $^{123}$I, $^{131}$I, $^{67}$Ga and $^{111}$In labeled compounds with corresponding $^{99m}$Tc labeled compounds when possible. Due to favorable physical characteristics as well as extremely low price ($0.21/mCi), $^{99m}$Tc has been preferred to label radiopharmaceuticals.

A number of factors must be considered for optimal radioimaging in humans. To maximize the efficiency of detection, a valent metal ion that emits gamma energy in the 100 to 200 keV range is preferred. A "gamma emitter" is herein defined as an agent that emits gamma energy of any range. One of ordinary skill in the art would be familiar with the various valent metal ions that are gamma emitters. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is a preferred radionuclide because it emits gamma radiation at 140 keV, it has a physical half-life of 6 hours, and it is readily available on-site using a molybdenum-99/technetium-99m generator. One of ordinary skill in the art would be familiar with methods to determine optimal radioimaging in humans.

In other embodiments of the compounds of the present invention, including compounds suitable for dual chemotherapy and radiation therapy, the chelator moiety may be chelated to a therapeutic radionuclide. For example, in some embodiments of the present invention, the therapeutic radionuclide is a beta-emitter. As herein defined, a beta emitter is any agent that emits beta energy of any range. Examples of beta emitters include Re-188, Re-186, Ho-166, Y-90, Bi-212, Bi-213, and Sn-153. The beta emitters may or may not also be gamma emitters. One of ordinary skill in the art would be familiar with the use of beta emitters in the treatment of hyperproliferative disease, such as cancer.

In further embodiments of the compounds of the present invention, the valent metal ion is a therapeutic metal ion that is not a beta emitter or a gamma emitter. For example, the therapeutic metal ion may be platinum, cobalt, copper, arsenic, selenium and thallium. Compounds including these therapeutic metal ions may be applied in the methods of the present invention directed to the treatment of hyperproliferative disease, such as the treatment of cancer. Methods of performing dual chemotherapy and radiation therapy that involve the compounds of the present invention are discussed in greater detail below.

G. METHODS OF SYNTHESIS

1. Source of Reagents for the Compounds of the Present Invention

Reagents for preparation of the compounds of the present invention can be obtained from any source. A wide range of sources are known to those of ordinary skill in the art. For example, as set forth below in the examples below, glucosamine based carbohydrate can be obtained from the hydrolysis of chitosan, chondroitin, hyaluronate in 40% sodium hydroxide. The reagents can be synthetic, or obtained from natural sources. Reagents can be of any purity. For example, reagents may be isolated and purified using any technique known to those of ordinary skill in the art. For example, carbohydrates of a particular molecular weight can be isolated using particular dialysis membranes.

2. Conjugation of a Diagnostic Moiety, Therapeutic Moiety, or Tissue Targeting Moiety to an Carbohydrate Any method known to those of ordinary skill in the art can be used to conjugate a diagnostic moiety, therapeutic moiety, or tissue targeting moiety to a carbohydrate moiety of the saccharide backbone of the claimed compounds. Chemical groups with acid moieties such as folic acid or diatriozoic acid may be conjugated to the amino group of oligosacchrides such as poly(glucosamine), or chitosan. Chemical groups with amino or hydroxyl moieties such as doxorubicin or paclitaxel may be conjugated to the acid moieties of carbohydrates such as chondroitin or hyaluranate. Metallic substances such as gadolinium, gallium, rhenium, technetium or platinum may be chelated to carbohydrate with or without chelators. The formal chelates provide better stability. The reaction can be carried out in an aqueous medium or a non-aqueous medium. Most preferably, the conjugation is carried out in an aqueous medium. Any ratio of reagents can be used in the reaction mixture. For example, in some embodiments the ratio of carbohydrate to moiety is 1:1 in water. The different ratio may change the solubility and viscosity in aqueous solution. In some embodiments of the present methods, a coupling agent is used to couple the diagnostic, therapeutic, or tissue targeting moiety to an oligosaccharide monomer, wherein the monomer comprises from about 2 to about 7 carbohydrate residues. In certain embodiments, the coupling agent used in aqueous condition is 1-ethyl-3-(3-dimethylaminopropyl) carbodiimide-HCl (EDC). Other examples of the coupling agent used in nonaqueous condition is 1,3-dicyclohexylcarbodiimide (DCC). In some embodiments of the present methods, the diagnostic, therapeutic, or tissue targeting moiety can first be dissolved in water. The aqueous solution comprising the diagnostic, therapeutic, or tissue targeting moiety can then be added to an aqueous solution comprising the oligosaccharide monomer. The reaction mixture can then be stirred for 25 hours at room temperature. The product can then be isolated from solution by any method known to those of ordinary skill in the art. For example, the product can be dialyzed from solution using a dialysis membrane that has a cut-off at 5,000 daltons. The product can then be used immediately, or freeze-dried and stored.

Conjugation of the diagnostic, therapeutic, or tissue targeting moiety can be to any residue of a carbohydrate moiety of the saccharide backbone In certain preferred embodiments, the conjugation is to an amine or an acid groups.

More than one type of therapeutic, diagnostic, or tissue-targeting moiety can be conjugated to the saccharide backbone. For example, in certain embodiments, a therapeutic and tissue targeting moiety are conjugated to a carbohydrate moiety of the backbone structure. Therapeutic agents, such as methotrexate or doxorubicin, can be conjugated the amino or acid moieties of the saccharide backbone. Diagnostic agents such as diatrizoic acid, iothalmic acid, and iopanoic acid can be conjugated to the amino or acid moieties backbone. Tissue targeting moieties such as hypoxic markers (metronidazole, misonidazole), glycolysis markers (carbohydrate), amino acids (e.g., tyrosine, lysine), cell cycle markers (e.g., adenosine, guanosine), or receptor markers (e.g., estrogen, folate, androgen) can be conjugated to the amino or acid moieties of the saccharide backbone. In other embodiments, two or more different therapeutic or diagnostic moieties are conjugated to the same saccharide backbone. For example, in certain embodiments, a diagnostic agent (e.g., x-ray contrast media or optical contrast media) and a radiometallic substance are both conjugated. It may be employed for PET/CT, SPECT/CT, or optical/CT applications. For example, in certain embodiments, a radioactive agent or optical contrast agent and a non-radioactive metallic substance (e.g., gadolinium, iron, or manganse) are both conjugated to the same backbone structure. It may be employed in any forms of imaging, including PET/MRI, SPECT/MRI, or optical/MRI applications. For example, in certain embodiments, a therapeutic agent and a radiotherapeutic metallic substance are conjugated to the same saccharide backbone structure. Such agents may be employed for radiochemotherapy.

3. Conjugation of Chelator Moiety to a Carbohydrate Moiety

Any method known to those of ordinary skill in the art can be used to conjugate a chelator moiety to a carbohydrate residue. In certain particular embodiments, a carbohydrate is first conjugated with one or more diagnostic, therapeutic, or tissue-targeting moieties which is performed in the manner as set forth above.

For example, an aqueous solution of the carbohydrate conjugated to the therapeutic, diagnostic, or tissue targeting moiety is prepared. To this solution, sodium bicarbonate can be added, together with a coupling agent and one or more chelator agents to be coupled to the carbohydrate. The reaction mixture can be stirred at room temperature for any period of time, such as 24 hours. The chelator moiety—carbohydrate—therapeutic/diagnostic/tissue targeting moiety conjugate can then be isolated from solution using any method known to those of skill in the art. For example, in some embodiments, the product is isolated from solution by dialysis. In some embodiments, the reaction mixture is dialyzed for 48 hours with a cut-off at a molecular weight of 5,000 and then freeze-dried. As set forth above, the resulting compound of the present invention can either be used immediately, or stored for later use.

In other embodiments, the chelator and the diagnostic, therapeutic, or tissue-targeting moiety are conjugated to the carbohydrate in the same reaction mixture using a coupling agent. Any coupling agent known to those of ordinary skill in the art can be used. For example, in certain particular embodiments, the coupling agent is 1-ethyl-3-(3-dimethylaminopropyl) carbodiimide-HCl (EDC) for aqueous condition and 1,3-dicyclohexylcarbodiimide (DCC) for nonaqueous condition.

4. Radiolabeling of Compounds of the Claimed Invention

Any method of radiolabeling known to those of ordinary skill in the art can be used to radiolabel any of the compounds of the present invention. In some embodiments of the present invention, for example, the chelate-carbohydrate-therapeutic/diagnostic/tissue targeting moiety conjugate is dissolved in water, and then tin(II) chloride solution added. The radiolabel (e.g., Na $^{99m}$TcO$_4$ or Na $^{186/188}$ReO$_4$) can then be added. Other metals (gallium chloride, gadolinium chloride, copper chloride, cobolt chloride, platinum) may not require tin(II) chloride solution. Any method known to those of ordinary skill in the art can be used to measure radiochemical purity. For example, it may be measured using thin layer chromatography (TLC) eluted with methanol:ammonium acetate (1:4).

Any method known to those of ordinary skill in the art can be used to isolate the radiolabeled conjugate from solution. For example, in some embodiments, the reaction mixture can be evaporated to dryness, and then later reconstituted in water for use.

H. IMAGING MODALITIES AND IMAGING AGENTS

Certain embodiments of the present invention pertain to methods of imaging a subject using a first imaging modality and a second imaging modality following administration of a composition comprising one of the conjugates set forth herein. Any imaging modality known to those of ordinary skill in the art is contemplated by the present invention. Examples of imaging modalities are set forth as follows.

1. Examples of Imaging Modalities

Certain embodiments of the present invention pertain to methods of imaging a subject using a first imaging modality and a second imaging modality that involve administering to the subject a composition comprising a diagnostically effect amount of one of the compounds of the present invention. Any imaging modality known to those of ordinary skill in the art is contemplated by the present invention. For example, in certain embodiments, the first imaging modality and the second imaging modality are selected from the group that includes PET, CT, SPECT, MRI, optical imaging, and ultrasound. Other examples of imaging modalities include digital subtraction angiography and x-ray angiography.

a. Computerized Tomography (CT)

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent (see, e.g., Henson et al., 2004). For example, gadopentate agents has been used as a CT contrast agent (discussed in Strunk and Schild, 2004).

b. Magnetic Resonance Imaging (MRI)

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

c. PET and SPECT

Imaging modalities that provide information pertaining to information at the cellular level, such as cellular viability, include positron emission tomography (PET) and single-photon emission computed tomography (SPECT). In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits high-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}C$, $^{13}N$, $^{15}O$, $^{18}F$, $^{82}Rb$, $^{62}Cu$, and $^{68}Ga$. SPECT radiopharmaceuticals are commonly labeled with positron emitters such as $^{99m}Tc$, $^{201}Tl$, and $^{67}Ga$. Regarding brain imaging, PET and SPECT radiopharmaceuticals are classified according to blood-brain-barrier permeability, cerebral perfusion and metabolism receptor-binding, and antigen-antibody binding (Saha et al., 1994). The blood-brain-barrier SPECT agents, such as $^{99m}TcO4$-DTPA, $^{201}Tl$, and [$^{67}Ga$]citrate are excluded by normal brain cells, but enter into tumor cells because gof altered BBB. SPECT perfusion agents such as [$^{123}I$]IMP, [$^{99m}Tc$]HMPAO, [$^{99m}Tc$]ECD are lipophilic agents, and therefore diffuse into the normal brain. Important receptor-binding SPECT radiopharmaceuticals include [$^{123}I$]QNE, [$^{123}I$]IBZM, and [$^{123}I$]iomazenil. These tracers bind to specific receptors, and are of importance in the evaluation of receptor-related diseases d. Optical Imaging Optical imaging is another imaging modality that has gained widespread acceptance in particular areas of medicine. Examples include optical labelling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

e. Ultrasound

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues, and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

2. Procedure for Dual Imaging

For example, as set forth above, the imaging modality may include, but are not limited to, CT, MRI, PET, SPECT, ultrasound, or optical imaging. Other examples of imaging modalities known to those of ordinary skill in the art are contemplated by the present invention.

The imaging modalities are performed at any time during or after administration of the composition comprising the diagnostically effective amount of the compound that comprises a carbohydrate conjugated to two imaging moieties. For example, the imaging studies may be performed during administration of the dual imaging compound of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times.

The second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. In certain embodiments of the present invention, the first and second imaging modalities are performed concurrently such that they begin at the same time following administration of the One of ordinary skill in the art would be familiar with performance of the various imaging modalities contemplated by the present invention.

In some embodiments of the present methods of dual imaging, the same imaging device is used to perform a first imaging modality and a second imaging modality. For example, in certain embodiments, diagnostic agent (x-ray contrast media or optical contrast) and radiometallic substance are conjugated to the same carbohydrate. It may be employed for PET/CT, SPECT/CT, or optical/CT applications. For example, in certain embodiments, radioactive agent or optical contrast and non-radioactive metallic substance (gadolinium, iron, manganse) are conjugated to the same carbohydrate. It may be employed for PET/MRI, SPECT/MRI, or optical/MRI applications. For example, in certain embodiments, a therapeutic agent and a radiotherapeutic metallic substance are conjugated to the same carbohydrate. It may be employed for radiochemotherapy. In other embodiments, a different imaging device is used to perform the second imaging modality. One of ordinary skill in the art would be familiar with the imaging devices that are available for performance of a first imaging modality and a second imaging modality, and the skilled artisan would be familiar with use of these devices to generate images.

I. RADIOLABELED AGENTS

Certain embodiments of the present invention pertain to methods of synthesizing a radiolabeled imaging agent for dual imaging and methods of synthesizing therapeutic agents for dual chemotherapy and radiation therapy. Other embodiments of the present invention pertain to kits for preparing these radiolabeled agents. Radiolabeled agents, compounds, and compositions provided by the present invention are provided having a suitable amount of radioactivity. For example, in forming $^{99m}Tc$ radioactive complexes, it is generally preferred to form radioactive complexes in solutions containing radioactivity at concentrations of from about 0.01 millicurie (mCi) to about 300 mCi per mL.

The radiolabeled dual imaging agents provided by the present invention can be used for visualizing sites in a mammalian body. In accordance with this invention, the imaging agents are administered by any method known to those of ordinary skill in the art. For example, administration may be in a single unit injectable dose. Any of the common carriers known to those with skill in the art, such as sterile saline solution or plasma, may be utilized after radiolabeling for preparing the compounds of the present invention for injection. Generally, a unit dose to be administered has a radioactivity of about 0.01 mCi to about 300 mCi, preferably 10 mCi to about 200 mCi. The solution to be injected at unit dosage is from about 0.01 mL to about 10 mL.

After intravenous administration of a compound of the present invention that is an imaging agent, imaging of the organ or tumor in vivo can take place, if desired, in hours or even longer, after the radiolabeled reagent is introduced into a patient. In most instances, a sufficient amount of the administered dose will accumulate in the area to be imaged within about 0.1 of an hour. As set forth above, imaging may be performed using any method known to those of ordinary skill in the art. Examples include PET, SPECT, and gamma scintigraphy. In gamma scintigraphy, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

J. KITS

Certain embodiments of the present invention are generally concerned with kits for preparing a composition comprising a radiolabeled imaging agent for dual imaging or kits for preparing a composition comprising a radiolabeled agent for dual chemotherapy and radiation therapy. The kits include a sealed vial containing a predetermined quantity of a compound of the present invention and a sufficient amount of reducing agent to label the compound with a radionuclide. In some embodiments of the present invention, the kit includes a radionuclide. In certain further embodiments, the radionuclide is $^{99m}$Tc.

The kit may also contain conventional pharmaceutical adjunct materials such as, for example, pharmaceutically acceptable salts to adjust the osmotic pressure, buffers, preservatives, antioxidants, and the like.

In certain embodiments, an antioxidant and a transition chelator are included in the composition to prevent oxidation of the chelator moiety. In certain embodiments, the antioxidant is vitamin C (ascorbic acid). However, it is contemplated that any other antioxidant known to those of ordinary skill in the art, such as tocopherol, pyridoxine, thiamine, or rutin, may also be used. The components of the kit may be in liquid, frozen or dry form. In a preferred embodiment, kit components are provided in lyophilized form.

K. HYPERPROLIFERATIVE DISEASE

Certain aspects of the present invention are generally concerned with methods of treating hyperproliferative disease in a subject using a compound of the present invention. A hyperproliferative disease is herein defined as any disease associated with abnormal cell growth or abnormal cell turnover For example, the hyperproliferative disease may be cancer. The term "cancer" as used herein is defined as an uncontrolled and progressive growth of cells in a tissue. A skilled artisan is aware other synonymous terms exist, such as neoplasm or malignancy or tumor. Any type of cancer is contemplated for treatment by the methods of the present invention. For example, the cancer may be breast cancer, lung cancer, ovarian cancer, brain cancer, liver cancer, cervical cancer, colon cancer, renal cancer, skin cancer, head and neck cancer, bone cancer, esophageal cancer, bladder cancer, uterine cancer, stomach cancer, pancreatic cancer, testicular cancer, lymphoma, or leukemia. In other embodiments of the present invention, the cancer is metastatic cancer.

L. DUAL CHEMOTHERAPY AND RADIATION THERAPY ("RADIOCHEMOTHERAPY")

Certain embodiments of the present invention pertain to methods of treating a subject with a hyperproliferative disease that involve administering to the subject a composition comprising a therapeutically effective amount of a compound of the present invention that is a poly(glucosamine) comprising a therapeutic moiety. For example, in certain embodiments, the therapeutic moiety is an anticancer moiety. Therapeutic moieties are discussed in detail elsewhere in this specification.

For example, the chelator moiety may be chelated to a beta-emitter. As herein defined, a beta emitter is any agent that emits beta energy of any range. Examples of beta emitters include Re-188, Re-186, Ho-166, Y-90, and Sn-153. One of ordinary skill in the art would be familiar with these agents for use in the treatment of hyperproliferative disease, such as cancer.

One of ordinary skill in the art would be familiar with the design of chemotherapeutic protocols and radiation therapy protocols that can applied in the administration of the compounds of the present invention. As set forth below, these agents may be used in combination with other therapeutic modalities directed at treatment of a hyperproliferative disease, such as cancer. Furthermore, one of ordinary skill in the art would be familiar with selecting an appropriate dose for administration to the subject. The protocol may involve a single dose, or multiple doses. The patient would be monitored for toxicity and response to treatment using protocols familiar to those of ordinary skill in the art.

M. PHARMACEUTICAL PREPARATIONS

Pharmaceutical compositions of the present invention comprise a therapeutically or diagnostically effective amount of a dual imaging agent or dual therapeutic agent of the claimed invention. The phrases "pharmaceutical or pharmacologically acceptable" or "therapeutically effective" or "diagnostically effective" refers to molecular entities and compositions that do not produce an adverse, allergic or other untoward reaction when administered to an animal, such as, for example, a human, as appropriate. The preparation of therapeutically effective or diagnostically effective compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "a composition comprising a therapeutically effective amount" or "a composition comprising a diagnostically effective amount" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the present compositions is contemplated.

The compositions of the present invention may comprise different types of carriers depending on whether it is to be administered in solid, liquid or aerosol form, and whether it need to be sterile for such routes of administration as injection. The dual imaging agents and dual therapeutic agents of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual required amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a dual imaging agent or a dual therapeutic agent. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight to about 1000 mg/kg/body weight or any amount within this range, or any amount greater than 1000 mg/kg/body weight per administration.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The dual imaging agents and dual therapeutic agents of the present invention may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, carbohydrates, sodium chloride or combinations thereof.

Sterile injectable solutions are prepared by incorporating the radiolabeled ethylenedicysteine derivative in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

N. COMBINATIONAL THERAPY

It is an aspect of this invention that claimed agents for dual chemotherapy and radiotherapy can be used in combination with another agent or therapy method, preferably another cancer treatment. Treatment with the claimed dual therapeutic agent may precede or follow the other therapy method by intervals ranging from minutes to weeks. In embodiments where another agent is administered, one would generally ensure that a significant period of time did not expire between the time of each delivery, such that the agents would still be able to exert an advantageously combined effect on the cell. For example, it is contemplated that one may administer two, three, four or more doses of one agent substantially simultaneously (i.e., within less than about a minute) with the dual therapeutic agents of the present invention. In other aspects, a therapeutic agent or method may be administered within about 1 minute to about 48 hours or more prior to and/or after administering a dual therapeutic agent or agents of the present invention, or prior to and/or after any amount of time not set forth herein. In certain other embodiments, a dual therapeutic agent of the present invention may be administered within of from about 1 day to about 21 days prior to and/or after administering another therapeutic modality, such as surgery or gene therapy. In some situations, it may be desirable to extend the time period for treatment significantly, however, where several weeks (e.g., about 1 to 8 weeks or more) lapse between the respective administrations.

Various combinations may be employed, the claimed agent for dual chemotherapy and radiation therapy is derivative is "A" and the secondary agent, which can be any other therapeutic agent or method, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the dual therapeutic agents of the present invention to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the described arsenical agent. These therapies include but are not limited to additional chemotherapy, additional radiotherapy, immunotherapy, gene therapy and surgery.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Genes

In yet another embodiment, the secondary treatment is a gene therapy in which a therapeutic polynucleotide is administered before, after, or at the same time as the dual therapeutic agent. Delivery of the dual therapeutic agent in conjunction with a vector encoding a gene product will have a combined anti-hyperproliferative effect on target tissues.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

O. EXAMPLES

The following examples are included to demonstrate preferred embodiments of the invention. It should be appreciated by those of skill in the art that the techniques disclosed in the examples which follow represent techniques identified by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Oligosaccharide-Diatrizoate (OS-DZ) Conjugates

Glucosamine based oligosaccharide (OS) was prepared by hydrolysis of chitosan in 40% sodium hydroxide. After hydrolysis, the desired fraction of molecular weight was isolated using dialysis membrane. In a typical example, dialysis membrane with a molecular weight cut off at 10,000 daltons was used. After 24 hours of dialysis, the solution was lyophilized and the product obtained was a light brownish powder. Conjugation of diatrizoate (a CT contrast media) to OS was conducted by using a drug:OS molar ratio of 1:1 in water. 1-ethyl-3-(3-dimethylaminopropyl) carbodiimide-HCl (EDC) was used as a coupling agent. In a typical run, diatrizoate (0.9 g, 1.4 mmol) was dissolved in water (6 ml), and EDC (324 mg, 1.7 mmol) was added. This mixture was then added to OS (1 g in 10 ml water). The reaction was stirred for 24 hours under room temperature. After dialysis (cut off at 5,000 daltons) against distilled water, the product was freeze-dried and weighed; 0.64 g. The product contained 35% DZ determined by UV at 238 nm. A synthetic scheme of conjugating EC and DZ to OS is shown in FIG. 1.

Example 2

Synthesis of Ethylenedicysteine-Oligosaccharide-Diatrizoate (EC-OS-DZ) Conjugates OS-DZ (460 mg, 35% DZ) was dissolved in 4 ml water. To this brownish solution, sodium bicarbonate (1N, 1 ml) was added to a stirred solution of EC (69 mg, 0.25 mmol) and EDC (98 mg, 0.5 mmol). The mixture was stirred at room temperature for 24 hours. The mixture was dialyzed for 48 hours with a cut-off at MW of 5,000 daltons. After dialysis, the product was freeze dried. The resulting product weighed 350 mg.

Example 3

Synthesis of EC-OS-Methotrexate

Figure 2:
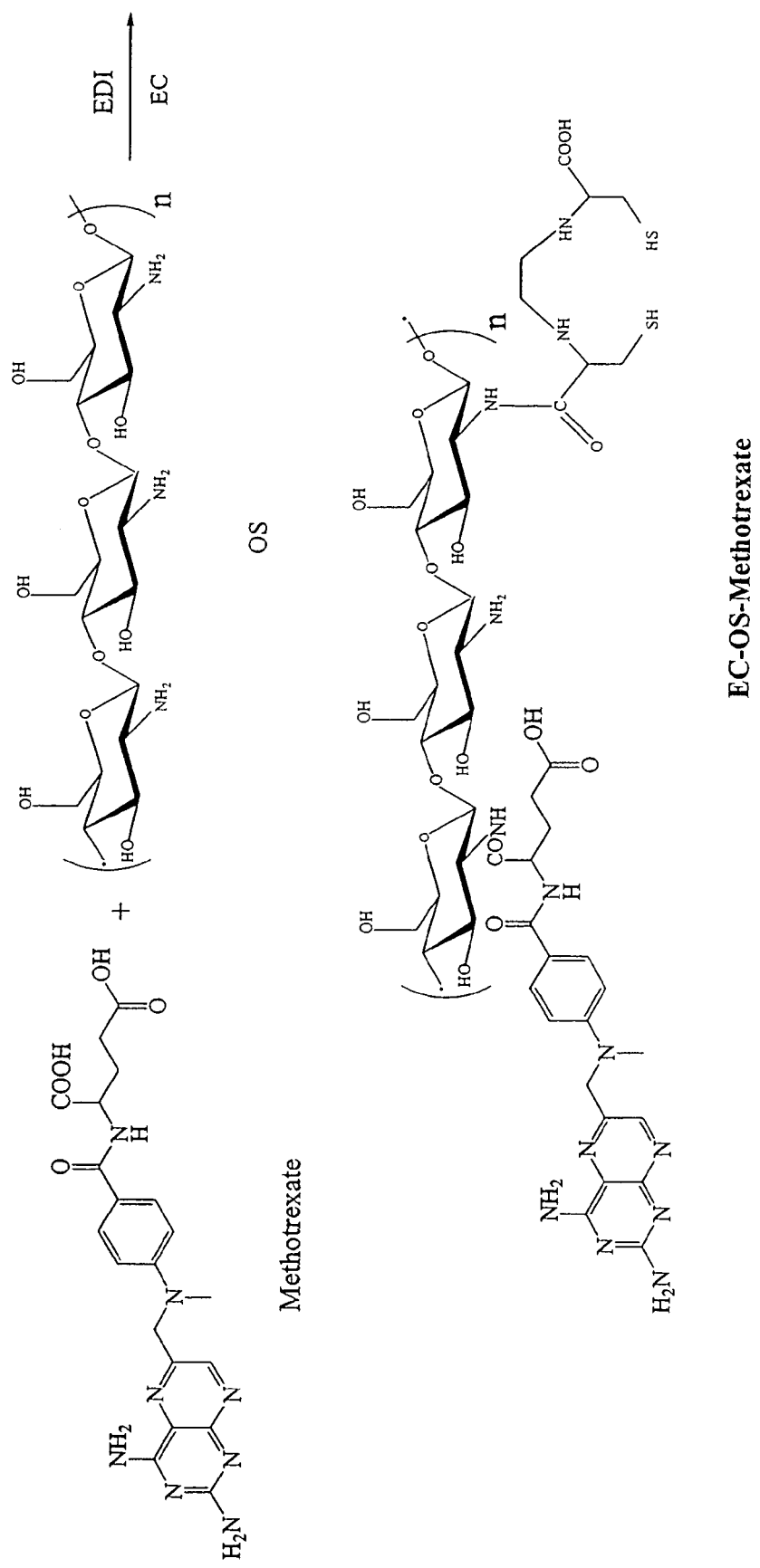
FIG. 2. Chemical synthesis of EC-OS-Methotrexate.
Figure 3:
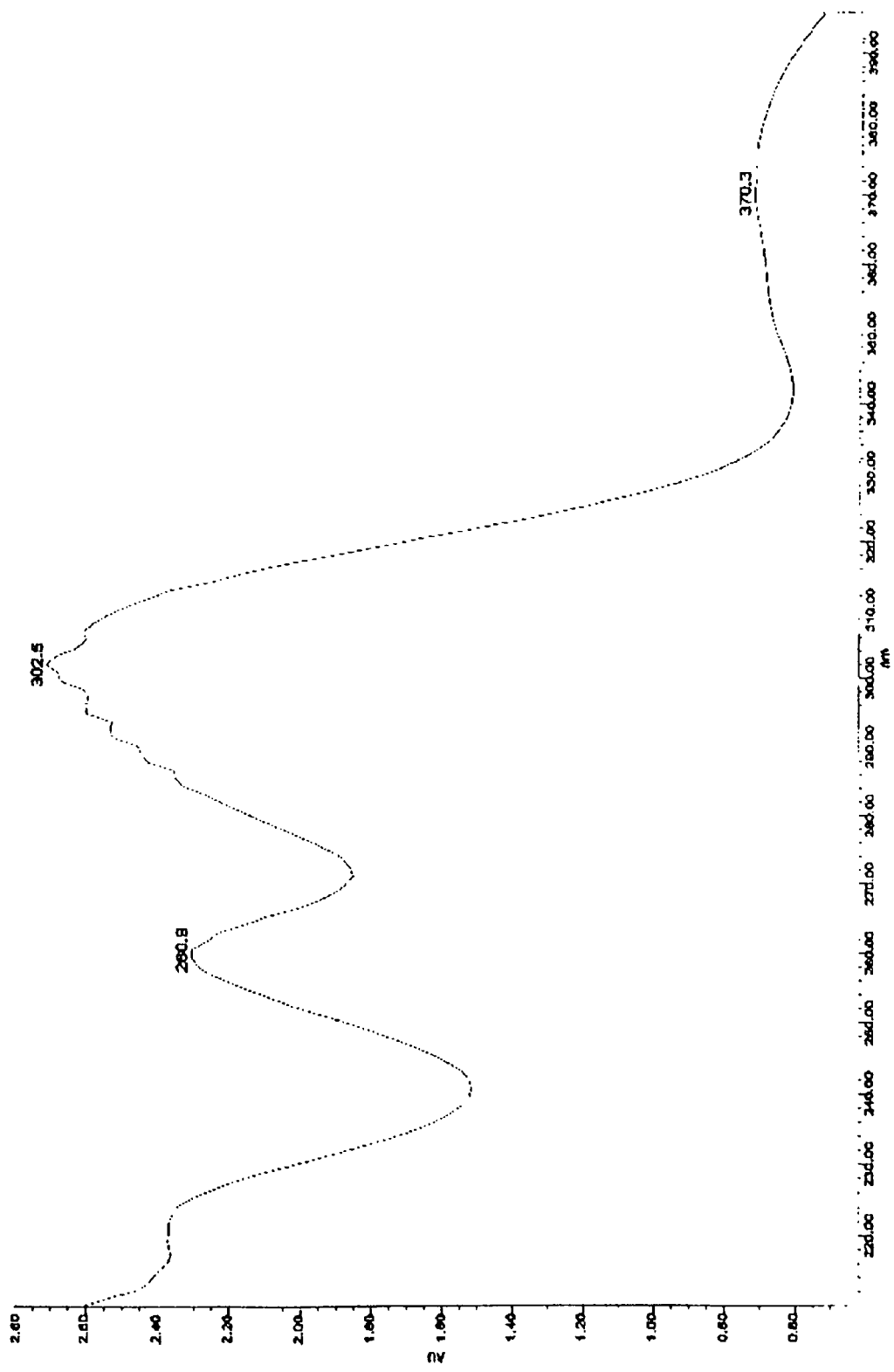
FIG. 3. UV spectra of methotrexate (MTX)
Figure 4:
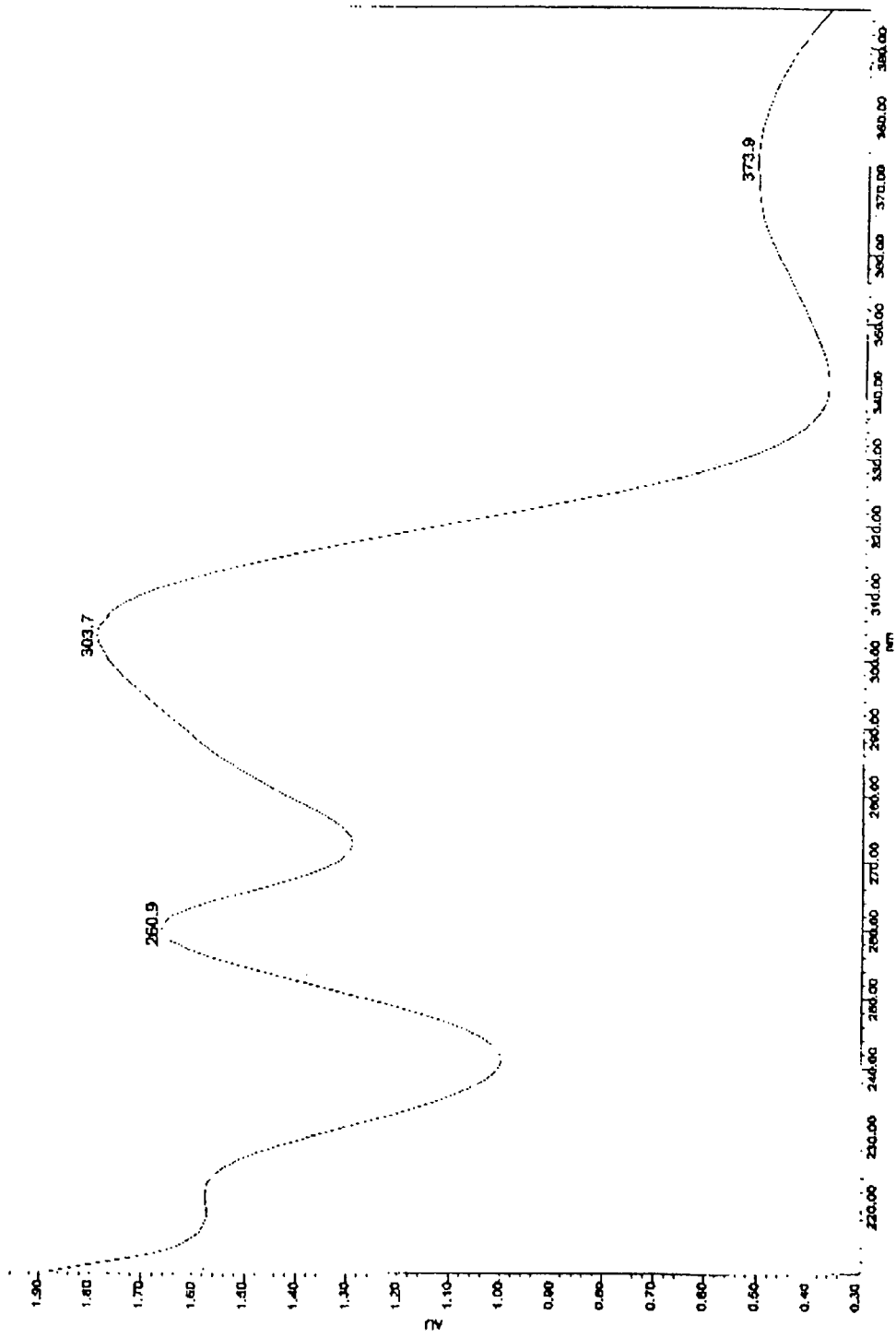
FIG. 4. UV spectra of EC-OS$_2$-MTX
Figure 5:
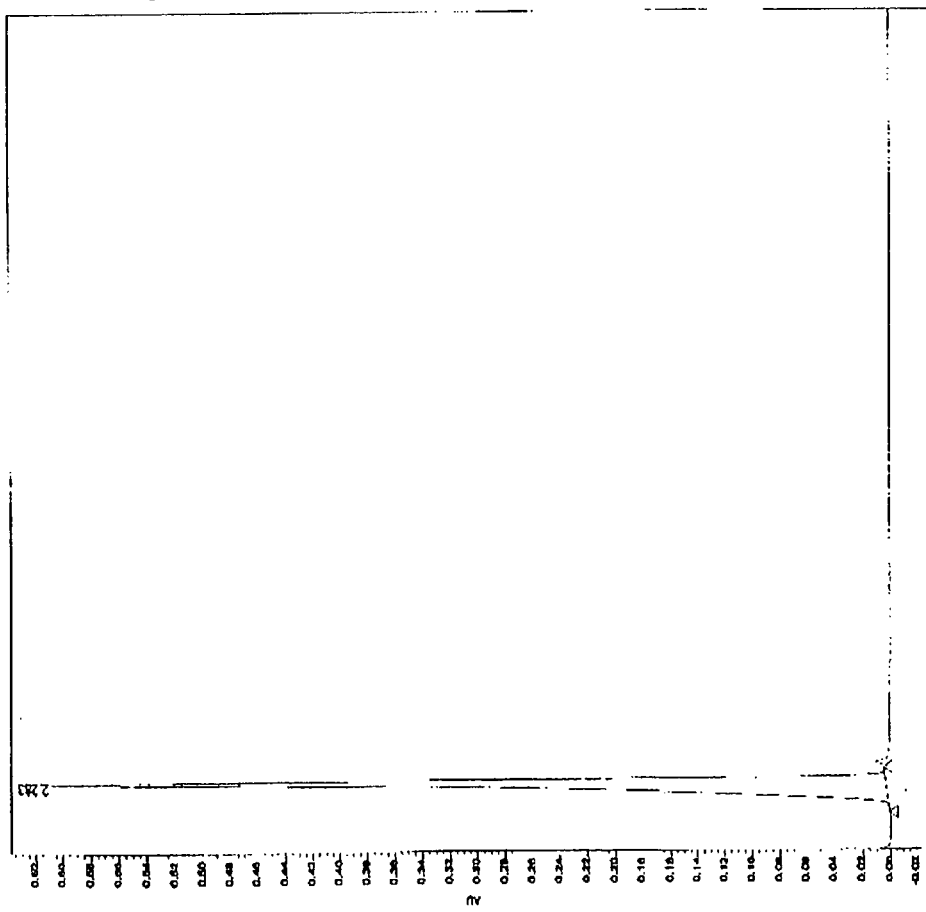
FIG. 5. HPLC chromatogram of MTX. Mobile phase—water (60%); acetonitrile (40%); flow rate 1 ml/min; column C18, 4.6×250 mm.
Figure 6:
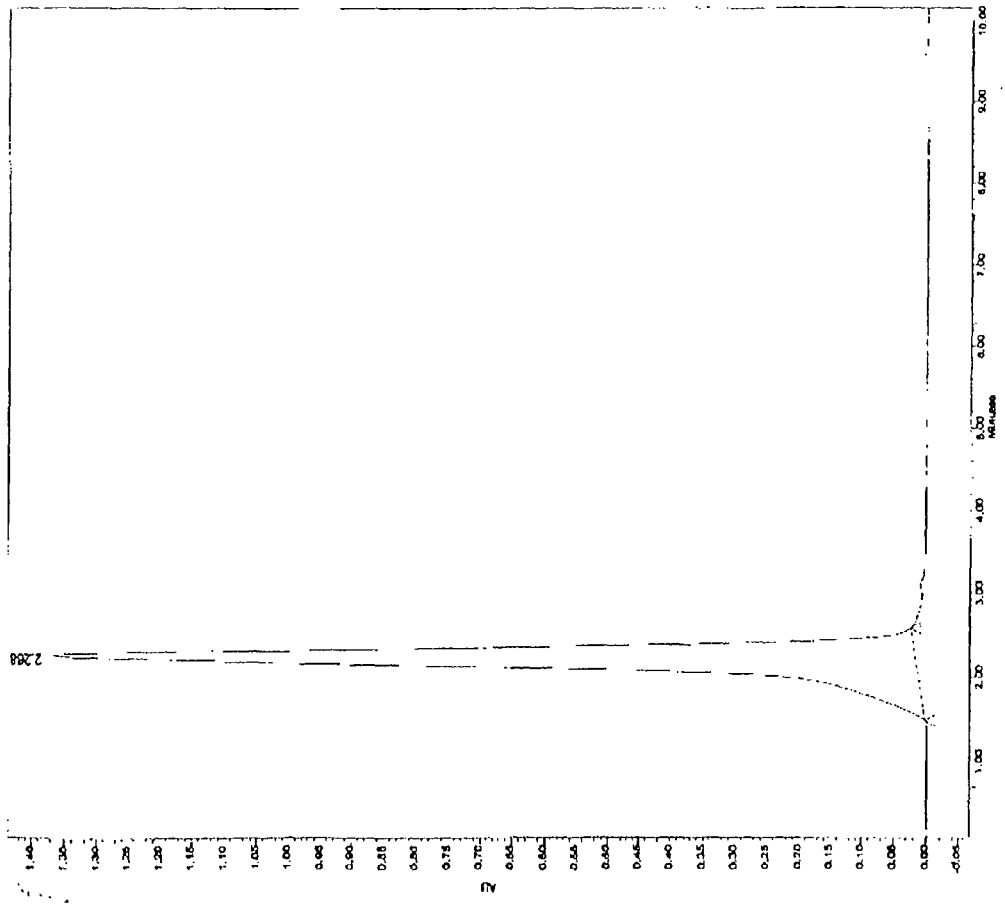
FIG. 6. HPLC chromatograph of EC-OS-MTX (28% w/w MTX eq). Mobile phase—water (60%), acetonitrile (40%); flow rate: 1 ml/min; column C18, 4.6×250 mm.

Conjugation of methotrexate (MTX) to OS was conducted by using a drug:OS molar ratio of 1:2 in water, similar to OS-DZ. In a typical run, MTX (0.5 g, 0.98 mmol) was dissolved in sodium hydroxide (1N, 3.4 ml), and EDC (470 mg, 2.45 mmol) was added. This mixture was then added to OS (1 g) in 5 ml water. The reaction was stirred for 24 hours under room temperature. After dialysis (cut off at 5,000 dalton against distilled water), the product was freeze-dried and weighed. The resulting product weighed 700 mg. The product contained 28% MTX determined by UV at 370 nm. 10% (w/w) of EC was then conjugated to OS-methotrexate in a manner similar to EC-OS-DZ. A synthetic scheme of conjugating EC and MTX to OS is shown in FIG. 2.

Example 4

Radiolabeling of EC-OS-DZ

EC-OS-DZ (5-300 mg) was dissolved in 0.2-0.8 ml water. Tin(II) chloride solution (0.1 ml, 1 mg/ml) was added. Sodium pertechnetate (Na $^{99m}$TcO$_4$, 37-370 MBq, Mallinckrodt, Houston, Tex.), was added. Finally, water was added to this solution to adjust the volume to 1 ml. Radiochemical purity was determined by TLC (ITLC SG, Gelman Sciences, Ann Arbor, Mich.) eluted with methanol:ammonium acetate (1:4). From radio-TLC analysis (Bioscan, Washington, D.C.), the radiochemical purity was more than 97%. For $^{68}$Ga-labeling, $^{68}$Ga was eluted from a $^{68}$Ge/$^{68}$Ga generator (Isotope Products Laboratories, Valencia, Calif.) using 1N HCL. The acidic solution was evaporated to dryness with either GaCl$_3$ carrier added or no carrier added. The solution was reconstituted in water. EC-OS-DZ (5-300 mg) dissolved in 0.2-0.8 ml water was then added to the radioactive solution. Finally, water was added to this solution to adjust the volume to 1 ml.

Example 5

Scintigraphic Imaging Studies

Female Fischer 344 rats (150±25 g) (Harlan Sprague-Dawley, Indianapolis, Ind.) were inoculated subcutaneously with 0.1 ml of mammary tumor cells from the 13762 tumor cell line suspension ($10^6$ cells/rat, a tumor cell line specific to Fischer rats) into the hind legs. Imaging studies were performed 12 to 15 days after inoculation. Tumor sizes approximately 1-1.5 cm were measured. Scintigraphic images were obtained using a m-camera from Siemens Medical Systems (Hoffman estates, Ill.). The camera was equipped with a low-energy parallel-hole collimator. The field of view is 53.3 cm×38.7 cm. The intrinsic spatial resolution is 3.2 mm and the pixel size is 19.18 mm (32×32, zoom=1) to 0.187 mm (1024×1024, zoom=3.2). With a low-energy, high-resolution collimator (as required with $^{99m}$Tc), the system is designed for a planar sensitivity of at least 172 counts/minute (cpm)/μCi and spatial resolution of 4-20 mm. UPET or autoradiography was used for PET imaging studies (0.5 mCi/rat). Planar scintigraphy was obtained at immediate, 0.5-4 hours after i.v. injection of $^{99m}$Tc-EC-OS-DZ (0.25 mCi/rat, 100 mg DZ equivalent/rat). The ROIs (region of interest in counts per pixel) count between tumor and muscle was used to calculate tumor-to-nontumor ratios. An autoradiogram was obtained at 1 hour post-administration of $^{68}$Ga-EC-OS-DZ. To demonstrate EC-OS-DZ (a functional CT contrast media) accumulates in the tumor, x-ray was performed at various time point after i.v. injection of DZ and EC-OS-DZ (300 mg/rat, 100 mg DZ equivalent/rat).

Example 6

Conjugation of EC and Drugs to Oligosaccharide

Conjugation of EC and the drugs set forth in the previous examples to OS was performed in water along with a coupling agent (carbodiimide). The drug-to-OS ratios were in the range of 1:1 to 1:4. The drug content was in the range of 20-45% (w/w) determined by UV analysis. 10% (w/w) EC was then conjugated to OS-drug conjugate. The product could be isolated using a simple dialysis technique. HPLC analysis of MTX and EC-OS-MTX is shown in FIGS. 3-6. The conjugation yield of MTX equivalent was 28% (w/w).

Example 7

Dual Imaging Evaluation

Figure 7:
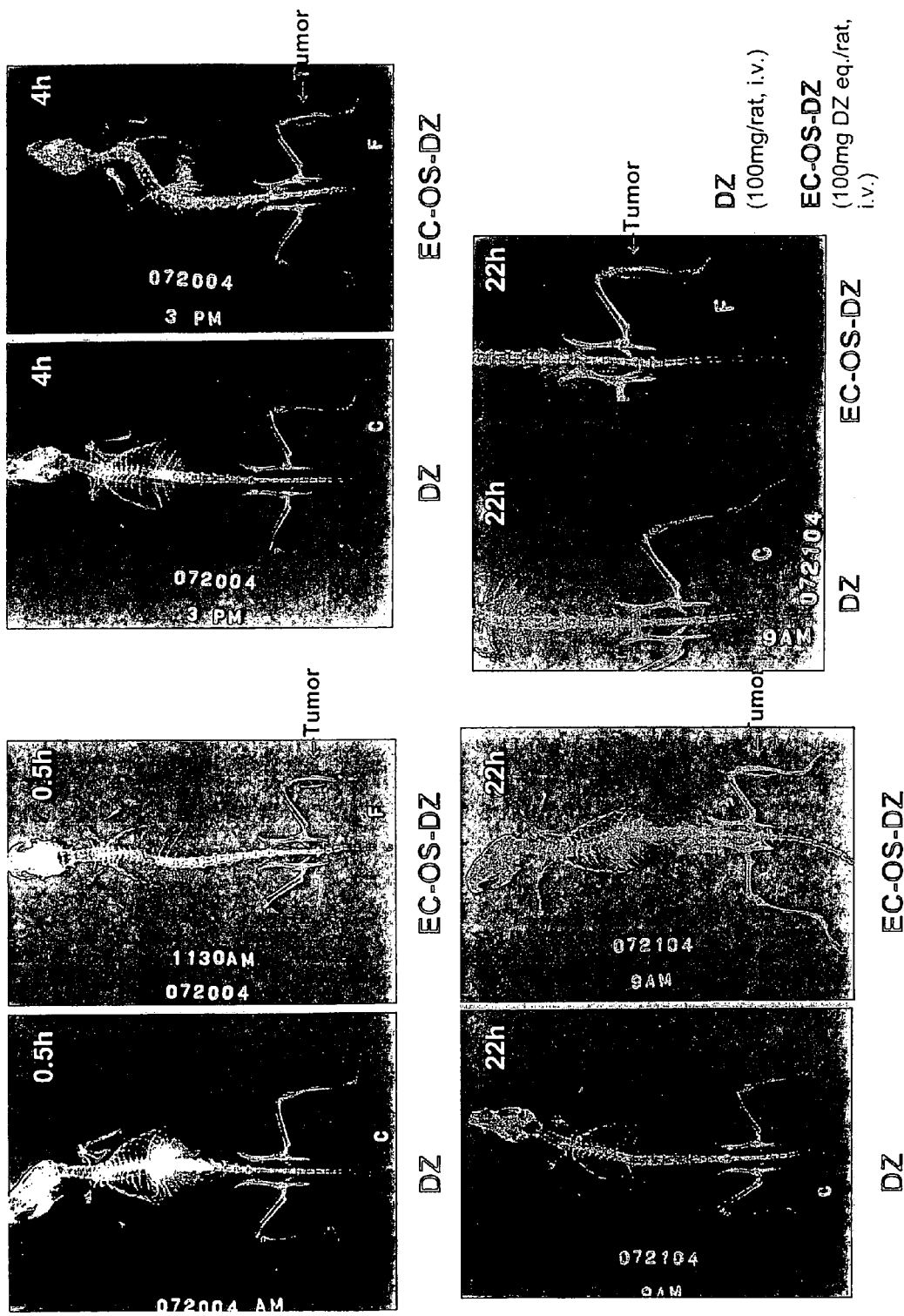
FIG. 7. X-ray of breast tumor-bearing rats receiving DZ (C) and EC-OS-DZ (F). Dose of DZ was 100 mg/rat, i.v.; dose of EC-OSo-DZ was 100 mg DZ eq./rat, i.v.
Figure 8:
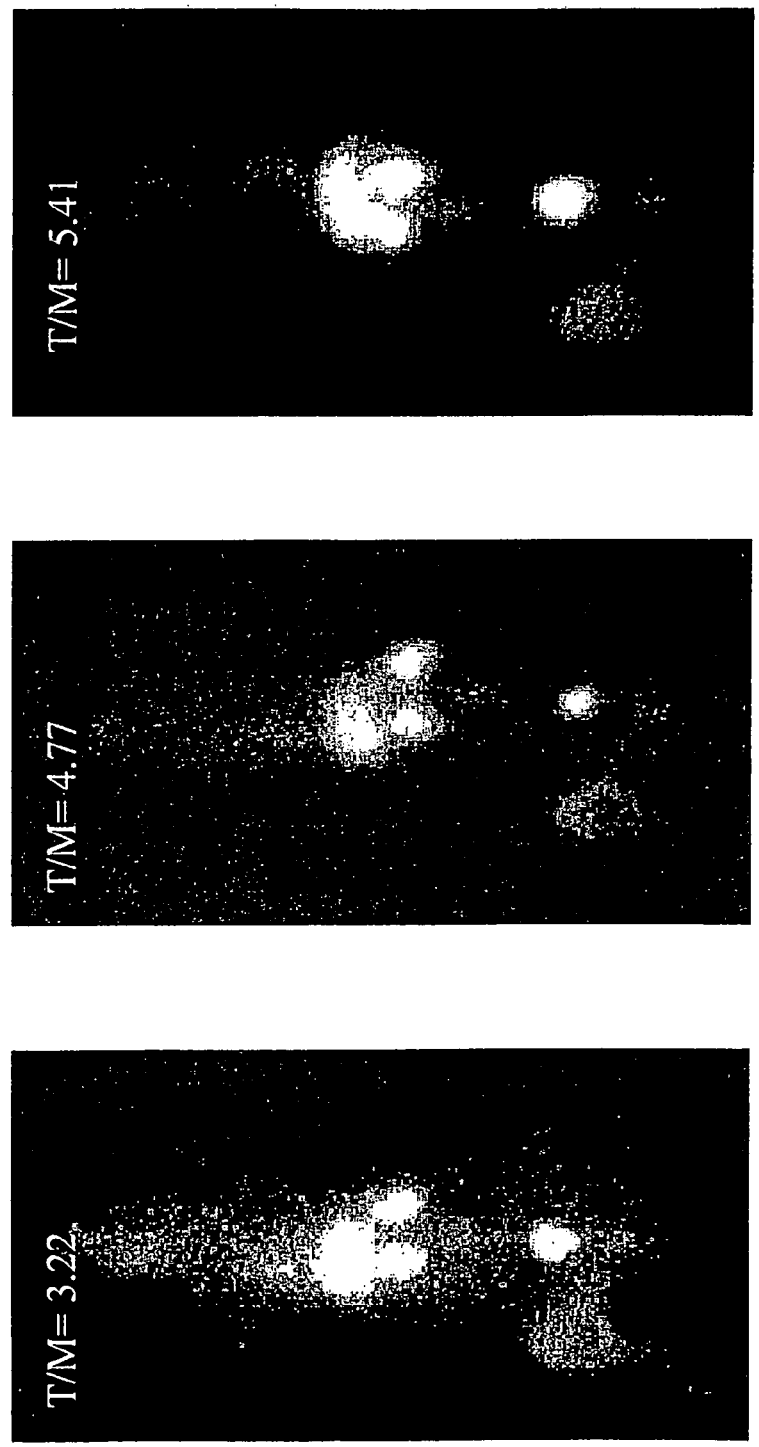
FIG. 8. Imaging of $^{99m}$Tc-EC-OS$_2$-DZ. Planar scintigraphy of $^{99m}$Tc-EC-OS$_2$-DZ in a breast tumor bearing rat (250 µCi/rat, i.v., acquired 500,000 count) showed tumor-to-nontumor ratios increased as a function of time. T=tumor; M=muscle.
Figure 9:
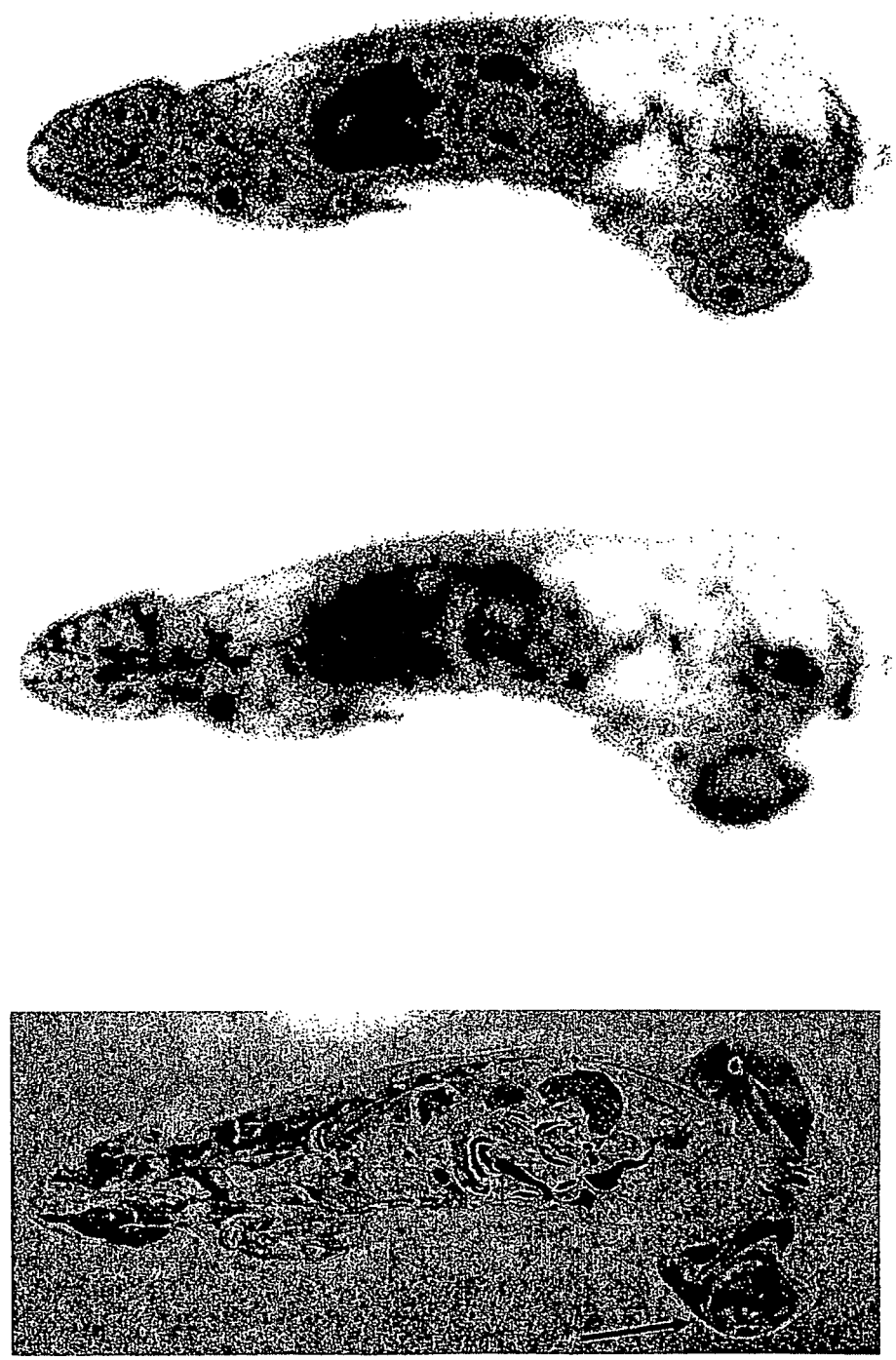
FIG. 9. Autoradiogram of $^{68}$Ga-EC-OS$_2$-DZ. A mammary tumor bearing rat was injected with 500 µCi of $^{68}$Ga-EC-OS$_2$-DZ and sacrificed 60 min post injection. Sections were cut at 100 µm and exposed for 16 hours. Arrow designates tumor site.

In the rat administered EC-OS-DZ at the single dose of 100 mg DZ equivalent/rat, there was a sustained uptake in the rat receiving the EC-OS-D compared to contrast media (DZ) (FIG. 7). In the same rat administered with $^{99m}$Tc-EC-OS-DZ, the tumor could be visualized by static planar imaging at 0.5-6 hrs (FIG. 8) and $^{68}$Ga-EC-OS-DZ at 1 hr by autoradiogram (FIG. 9). The findings indicate that EC-OS-DZ is a dual imaging agent for PET/CT and SPECT/CT.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,521,209
U.S. Pat. No. 6,692,724
U.S. Pat. No. 6,770,259
U.S. application Ser. No. 09/599,152
U.S. application Ser. No. 10/627,763
U.S. application Ser. No. 10/672,142
U.S. application Ser. No. 10/703,405
U.S. application Ser. No. 10/732,919
Alauddin and Conti, *Nucl. Med. Biol.*, 25:175-180, 1998.
Alauddin et al., *Nucl. Med. Biol.*, 23:787-792, 1996.
Alauddin et al., *Nucl. Med. Biol.*, 26:371-376, 1999.
Alberico et al., *Surg. Oncol. Clin. N. Am.*, 13(1):13-35, 2004.
Banner et al, *J. Natl. Cancer Inst.*, 88:140, 1994.
Blondeau et al., *Can. J. Chem.*, 45:49-52, 1967.
Bolhuis et al., *Int. J. Cancer Suppl.*, 7:78-81, 1992.
Bush et al., *Br. J. Cancer Suppl.*, 37(3):302-306, 1978.
Campbell et al., *Cancer Res.*, 51(19):5329-5338 1991.
Canevari et al., *Hybridoma.*, 12(5):501-507, 1993.
Chasselle et al, *Lancet*, 34B:143, 1995.
Coney et al., *Cancer Res.*, 54(9):2448-2455, 1994.
Deng and Lizzi, *Ultrasound Med. Biol.*, 28(3):277-286, 2002.
Dische, *Int. J. Radiat. Oncol. Biol. Phys.*, 20(1):147-152, 1991.
Forsberg et al., *Ultrasound Med. Biol.*, 23(8):1201-1208, 1997.
Franklin et al., *Int. J. Cancer Suppl.*, 8:89-95, 1994.
Gambhir et al., *J. Nucl. Med.*, 39:2003-2011, 1998.
Gambhir et al., *Proc. Natl. Acad. Sci. USA*, 96(5):2333-2338, 1999.
Gambhir et al., *Proc. Natl. Acad. Sci. USA*, 97:2785-2790, 2000.
Gatenby et al., *Int. J. Radiat. Oncol. Biol. Phys.*, 14(5):831-838, 1988.
Ginobbi et al., *Anticancer Res.*, 17(1A):29-35, 1997.
Goldberg et al., *Ultrasound Med. Biol.*, 20(4):319-333, 1994.
Goldberg, *Heart*, 78(3):209-210, 1997.
Gray et al., *Nature*, 182(4640):952-953, 1958.
Hall et al., *Radiat. Res.*, 114(3):415-424 1988.
Henson et al., *AJNR Am. J. Neuroradiol.*, 25(6):969-972, 2004.
Holm et al., *APMIS*, 102(6):413-419, 1994.
Holm, et al., *APMIS*, 102(11):828-836, 1994.
Hsueh and Dolnick, Biochem. Pharmacol., 45(12):2537-2545, 1993.
Iyer et al., *J. Nucl. Med.*, 42(1):96-105, 2001.
Koh et al., *Int. J. Radiat. Oncol. Biol. Phys.*, 22:199-212, 1992.
Kranz et al., *Proc. Natl. Acad. Sci USA*, 92(20):9057-9061 1995.
Leamon and Low, *Biochem. J.*, 291 (Pt 3):855-860, 1993.
Leamon and Low, *J. Biol. Chem.*, 267(35):24966-24971, 1992.
Leamon and Low, *J. Drug Target.*, 2(2):101-112, 1994.
Leamon and Low, *Proc. Natl. Acad. Sci. USA*, 88(13):5572-5576 1991.
Martin et al., *J. Nucl. Med.*, 30:194-201, 1989.
Medical Letter Handbook of Adverse Drug Interactions, 1995.
Medical Letter, 34:78; 34:79 1992.
Namavari et al., *Nucl. Med. Biol.*, 27:157-162, 2000.
Nordsmark et al., *Radiother. Oncol.*, 41(1):31-39, 1996.
Ophir and Parker, *Ultrasound Med. Biol.*, 15(4):319-333, 1989.
Orr et al., *J. Natl. Cancer Inst.*, 87(4):299-303, 1995.
Orr et al., *J. Natl. Cancer Inst.*, 87(4):299-303, 1995.
Patrick et al., *J. Neurooncol.*, 32(2):111-123, 1997.
PCT Appln. WO 2004/026344
Rasey et al., *Int. J. Radiat. Oncol. Biol. Phys.*, 17(5):985-991, 1989.
Rasey et al., *Radiother. Oncol.*, 17(2):167-173, 1990.
Ratner and Clarke, *J. AM Chem. Soc.*, 59:200-206, 1937.
Reed, *Cancer Cell*, 3:17-22, 2003.
Remington's Pharmaceutical Sciences, 18th Ed. Mack Printing Company, 1990.
Ross et al., *Cancer*, 73(9):2432-2443, 1994.
Saha et al., *Semin. Nucl. Med.*, 24(4):324-349, 1994.
Senner et al., *J. Natl. Cancer Inst.*, 88:140, 1994.
Strunk and Schild, *Eur. Radiol.*, 14(6):1055-1062, 2004.
Tjuvajev et al., *J. Nucl. Med.*, 43(8):1072-1083, 2002.
Valk et al., *J. Nucl. Med.*, 33(12):2133-2137, 1992.
Warrell, Jr et al, *N. Engl. J. Med.*, 329:177, 1993.
Weitman et al., *Cancer Res.*, 52(12):3396-3401 1992b.
Weitman et al., *Cancer Res.*, 52(23):6708-6711, 1992a.
Weitman et al., *J Neurooncol.*, 21(2):107-112, 1994.
Westerhof et al., *Cancer Res.*, 51(20):5507-5513, 1991.
Yaghoubi et al., *J. Nucl. Med.*, 42:1225-1234, 2001.
Yang et al., *Anticancer Res.*, 15:2479-2488, 1995.

What is claimed is:

1. A compound comprising
   (i) a poly(glucosamine) carbohydrate backbone that binds to endothelial cells,
   (ii) a first diagnostic moiety covalently attached to the carbohydrate backbone, the first diagnostic moiety selected from the group consisting of iothalamate, iohexol, diatrizoate, iopamidol, ethiodol, and iopanoate; and
   (iii) a second diagnostic moiety comprising an $N_2S_2$ chelator selected form the group consisting of DADS, ethylenedicysteine (EC) and DADT, conjugated to the carbohydrate backbone.

2. The compound of claim 1, wherein the compound is of formula (I):

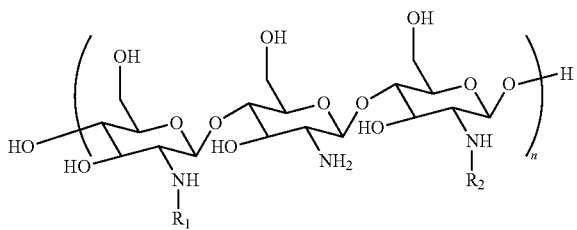

wherein $R_1$ is the first diagnostic moiety, $R_2$ is the second diagnostic moiety; or a stereoisomer of (I), or a combination of stereoisomers of (I), or a pharmaceutically acceptable salt of (I).

3. The compound of claim 1, wherein the carbohydrate backbone and the chelator comprise about 5% to about 50% by weight of the compound.

4. The compound of claim 1, wherein the first and second diagnostic moieties comprise from about 10% to about 50% by weight of the compound.

5. The compound of claim 1, wherein the chelator is ethylenedicysteine.

6. The compound of claim 1, further comprising a valent metal ion attached to the chelator.

7. The compound of claim 6, wherein the valent metal ion is selected from the group consisting of Tc-99m, Cu-60, Cu-61, Cu-62, Cu-67, In-111, Tl-201, Ga-67, Ga-68, As-72, Re-186, Re-188, Ho-166, Y-90, Sm-153, Sr-89, Gd-157, Bi-212, and Bi-213.

8. A compound of formula (II):
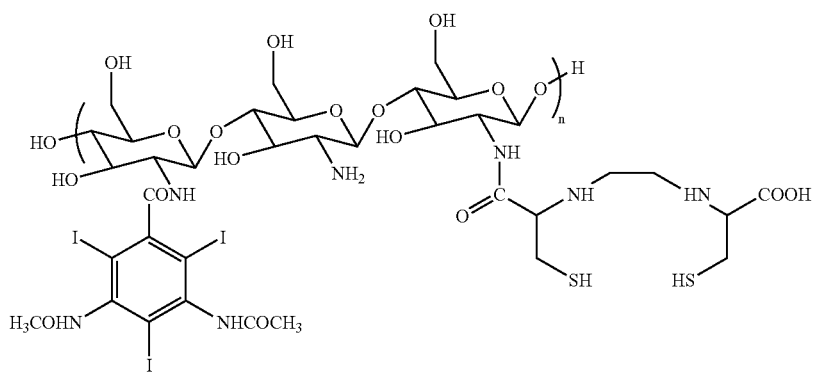
wherein n is an integer that is one or greater;
or a stereoisomer of (II), or a combination of stereoisomers of (II), or a pharmaceutically acceptable salt of (II).
9. The compound of claim 8, wherein n is about 1 to about 10,000.
10. The compound of claim 9, wherein the compound has a molecular weight of about 3,000 daltons to about 50,000 daltons.
* * * * *